US008115052B2

(12) United States Patent
Helentjaris

(10) Patent No.: US 8,115,052 B2
(45) Date of Patent: Feb. 14, 2012

(54) MODULATION OF ABSCISIC ACID

(75) Inventor: Tim Helentjaris, Ankeny, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 82 days.

(21) Appl. No.: 10/637,831

(22) Filed: Aug. 8, 2003

(65) Prior Publication Data

US 2004/0148654 A1    Jul. 29, 2004

Related U.S. Application Data

(63) Continuation of application No. 09/715,774, filed on Nov. 17, 2000, now abandoned.

(60) Provisional application No. 60/166,080, filed on Nov. 17, 1999.

(51) Int. Cl.
*C12N 15/82* (2006.01)
(52) U.S. Cl. ........................................ 800/278; 435/468
(58) Field of Classification Search ........................ None
See application file for complete search history.

(56) References Cited

U.S. PATENT DOCUMENTS 6,248,937 B1    6/2001    Finkelstein et al.

OTHER PUBLICATIONS

Leung et al., Science, 264:1448-1452, 1994.*
Guo et al., PNAS, 101: 9205-9210, 2004.*
Keskin et al., Protein Science, 13:1043-1055, 2004.*
Thornton et al. (Nature Structural Biology, structural genomics supplement, Nov. 2000).*
Gosti et al. (The Plant Cell, 11:1897-1909, 1999).*
Maniatis et al. (Molecular Cloning: A Laboratory Manual, Cold Spring Harbor Laboratory, 1982).*
Sheen (PNAS, 95:975-980, 1998).*
Parcy et al. (The Plant Cell, 6:1567-1582, 1994).*
Mambelli et al. (Physiologia Plantarum 104: 266-272, 1998).*
Bustos et al. (1998) "Induction of a β-phaseolin promoter by exogenous abscisic acid in tobacco: developmental regulation and modulation by external sucrose and $Ca^{2+}$ ions" *Plant Molecular Biology* 37:265-274.
Cutler et al. (1996) "A Protein Farnesyl Transferase Involved in Abscisic Acid Signal Transduction in *Arabidopsis*" *Science* 273:1239-1241.
Finkelstein et al. (1998) "The *Arabidopsis* Abscisic Acid Response Locus *AB14* Encodes an APETALA2 Domain Protein" *The Plant Cell* 10:1043-1054.
Giraudet et al. (1992) "Isolation of the *Arabidopsis AB13* Gene by Positional Cloning" *The Plant Cell* 4:1251-1261.
Himmelbach et al. (1998) "Signalling of Abscisic Acid to Regulate Plant Growth" *Phil. Trans. R. Soc. Lond. B* 353:1439-1444.
Hoecker et al. (1995) "Integrated control of seed maturation and germination programs by activator and repressor functions of Viviparous-1 and maize" *Genes and Development* 9:2459-2469.
Keddie et al. (1992) "Cloning and characterization of an oleosin gene from *Brassica napus*" *Plant Molecular Biology* 19(3):443-453.
Keddie et al. (1994) "A seed specific *Brassica napus* oleosin promoter interacts with a G-box-specific protein and may be bi-directional" *Plant Molecular Biology* 24(2):327-340.
Leung et al. (1998) "*Abscisic* Acid Signal Transduction" *Annu. Rev. Plant Physiol. Plant Mol. Biol.* 49:199-222.
Mambelli et al. (1998) "Inhibition of Maize Endosperm Cell Division and Endoreduplication by Exogenously Applied Abscisic Acid" *Physiologia Plantarum* 104:266-272.
McCarty et al. (1991) "The *Viviparous-1* Developmental Gene of Maize Encodes a Novel Transcriptional Activator" *Cell* 66:895-905.
Meyer et al. (1994) "A Protein Phosphatase 2C Involved in ABA Signal Transduction in *Arabidopsis thaliana*" *Science* 264:1452-1455.
Paek et al. (1998) "Inhibition of germination gene expression by Vivaprous-1 and ABA during maize kernel development" *Molecules and Cells* 8(3):336-342.
Parcy et al. (1994) "Regulation of gene expression programs during arabidopsis seed development; roles of the *AB13* locus and of endogenous abscisic acid" *The Plant Cell* 6:1567-1582.
Robinson et al. (1999) "Altered Resource Allocation During Seed Development in *Arabidopsis* Caused by the *abi3* Mutation" *Plant, Cell and Environment* 22(1):117-123.
Rodriguez et al. (1998) "ABI2, A Second Protein Phosphatase 2C Involved in Abscisic Acid Signal Transduction in *Arabidopsis*" *FEBS Letters* 421:185-190.
Gosti, F., et al., "ABI1 Protein Phosphatase 2C Is a Negative Regulator of Abscisic Acid Signaling," *The Plant Cell*, 1999, pp. 1897-1909, vol. 11.
Iuchi, S., et al., "Regulation of Drought Tolerance by Gene Manipulation of 9-cis-Epoxycarotenoid Dioxygenase, A Key Enzyme in Abscisic Acid Biosynthesis in *Arabidopsis*," *The Plant Journal*, 2001, pp. 325-333, vol. 27(4).
Leung, J., et al., "The *Arabidopsis* Abscisic Acid-Insensitive2 (ABI2) and ABI1 Genes Encode Homologous Protein Prosphatases 2C Involved in Abscisic Acid Signal Transduction," *The Plant Cell*, 1997, pp. 759-771, vol. 9.
Marris, E., "Plant Hormone Study Pulled," *Nature*, 2008, p. 683, vol. 456.
Pennisi, E., "Stressed Out Over a Stress Hormone," *Science*, 2009, pp. 1012-1013, vol. 324.
Qin, X. and J. Zeevaart, "Overexpression of a 9-cis-Epoxycarotenoid Dioxygenase Gene in *Nicotiana plumbaginifolia* Increases Abscisic Acid and Phaseic Acid Levels and Enhances Drought Tolerance," *Plant Physiology*, 2002, pp. 544-551, vol. 128.
Wang, X-F. and D-P. Zhang, "Abscisic Acid Receptors: Multiple Signal-Perception Sites," *Annals of Botany*, 2008, pp. 311-317, vol. 101.

* cited by examiner

*Primary Examiner* — Vinod Kumar
(74) *Attorney, Agent, or Firm* — Alston & Bird LLP

(57) ABSTRACT

Compositions and methods for modulating abscisic acid (ABA) perception and signal transduction in developing seed are provided. The methods and compositions find use in increasing yield in plants. Compositions comprise genetic constructs known to affect ABA sensitivity, particularly ABA biosynthetic mutants and fragments and variants thereof. Such compositions can be expressed with seed-preferred promoters.

4 Claims, No Drawings

MODULATION OF ABSCISIC ACID

CROSS-REFERENCE TO RELATED APPLICATIONS

This application is a continuation of U.S. application Ser. No. 09/715,774, filed Nov. 17, 2000, which claims the benefit of U.S. Provisional Application No. 60/166,080, filed Nov. 17, 1999, the contents of which are hereby incorporated by reference in their entirety.

FIELD OF THE INVENTION

The present invention is drawn to methods for the genetic modification of plants, particularly for modulating plant response to abscisic acid.

BACKGROUND OF THE INVENTION

Abscisic acid (ABA) is a phytohormone that plays an essential regulatory role for a variety of physiological processes. The phytohormone is involved in embryo development, seed dormancy, transpiration, and adaptation to environmental stresses. ABA regulates many agronomically important aspects of plant development including synthesis of seed storage proteins and lipids as well as regulating stomatal closure. The analysis of ABA-responsive promoters has revealed a diversity of potential cis-acting regulatory elements.

Mutations in ABA biosynthesis are known in a variety of plant species. See, for example, Leung and Giraudat (1998) *Annu. Rev. Plant Physiol. Plant Mol. Biol.* 49:199-222, and the references cited therein. In *Arabidopsis*, a number of genetically distinct *Arabidopsis* acid-insensitive loci have been identified. These mutants were selected based on the ability of seeds to germinate in the presence of inhibitory concentrations of ABA. The mutations have also been shown to affect several additional aspects of seed development, including accumulation of storage proteins and lipids, chlorophyll breakdown, and desiccation tolerance.

To date, numerous mutants and genes have been characterized in plants. Five mutationally identified ABA response loci have been cloned. These represent three classes of proteins. The classes include two orthologous transcriptional regulators (Viviparousl-Vp1) of maize and ABA-insensitive 3 of *Arabidopsis* (ABI3), two highly homologous members of the protein phosphotase 2C family, and a farnesyl transferase of *Arabidopsis*. See, for example, McCarty et al. (1991) *Cell* 66:895-905; Giraudat et al. (1992) *Plant Cell* 4:1251-1261; Leung et al. (1994) *Science* 264:1448-1452; Leung et al. (1997) *Plant Cell* 9:759-771; and Cuither et al. (1996) *Science* 273:1239-1241.

During the maturation phase of seed development, the embryo becomes quiescent in tissues that are destined to remain viable and the dry seed acquire tolerance to desiccation. In maize and other grasses, this includes cells in the aleurone layer of the seed endosperm. The viviparous mutants of maize are blocked in the maturation program. Thus, the mutant embryo proceeds precociously into seedling development while attached to the mother plant. The nine characterized vivipary loci affect early steps in the biosynthesis of carotenoids and abscisic acid. vp1 embryos exhibit reduced sensitivity to ABA in culture. It has been suggested that the initial Vp1 may encode a factor involved in ABA perception.

At the molecular level, embryonic maturation is associated with a broad range of gene activation. Many of the genes expressed are regulated by the hormone ABA. However, the molecular mechanisms of ABA action are largely unknown.

ABA mediated growth control is a fundamental response of plants to adverse environmental conditions. Because little is known about the molecular mechanism of ABA-mediated growth control, methods are needed to modulate the response of plants to ABA, particularly to increase yield.

SUMMARY OF THE INVENTION

Compositions and methods for increasing yield in plants, particularly seed plants, are provided. The methods involve modulating abscisic acid (ABA) perception and signal transduction in developing seed. Methods are useful for protecting plants against the harmful/detrimental effects of stress and adverse environmental conditions. Compositions comprise genetic constructs known to affect ABA sensitivity in a plant or plant cell. Of particular interest are ABA-associated sequences. Such sequences include mutants, fragments and variants thereof, as well as antisense nucleotide sequences, for genes and mutants involved in the perception and signal transduction of ABA. The DNA sequences may be provided in constructs for temporal, developmental, and tissue specificity.

Compositions are useful in methods for increasing yield in plants under stress, particularly abiotic stress. In this manner, detrimental effects of ABA on ear and kernel growth are ablated.

Transformed plants, plant cells, tissues, and seeds are additionally provided.

DETAILED DESCRIPTION OF THE INVENTION

Methods for modulating early plant response to abscisic acid (ABA) are provided, particularly to insulate crop yield by ablating the detrimental effects of ABA on seed development. In particular, the invention provides compositions and methods for disrupting ABA signaling or function. The compositions and methods are useful for disrupting ABA function in a tissue and developmental-preferred manner to insulate female reproductive tissue growth from stress and adverse environmental conditions.

For purposes of the invention "early plant response" is intended the development of reproductive tissue, seed development, endosperm development, and seed maturation. ABA is involved in many other physiological and developmental processes throughout the life cycle of plants, including seed dormancy, adaptation to abiotic environmental stresses, such as cold, drought, salinity, etc., accumulation of nutritive reserves, acquisition of desiccation tolerance, stomatal closure, and the like. In the early phases, the phytohormone ABA regulates seed maturation and the maintenance of embryo dormancy. Later, at the onset of ontogenesis, ABA mediates several adaptational responses towards environmental cues such as desiccation, cold, salt stress, and other stresses, and acts as a negative growth regulator. Generally, ABA imposes a bimodal growth control by regulating the potential of the cell to enlarge, possibly by turgor control, and by inducing mitotic growth arrest in plants in accordance with its role as a negative growth regulator.

The invention involves controlling or modulating the early response of the plant to the signaling of ABA. By "modulating" is intended the up-regulation or down-regulation of the plant response to ABA. For purposes of the invention, modulation is generally down-regulation by the disruption of ABA synthesis or the disruption of the perception and signal transduction of ABA. It is recognized that total disruption of ABA function in plants is not practical as ABA performs many useful roles in plant development. For purposes of the invention, it is generally preferable to disrupt the effects of ABA at the site of the eventual effect, i.e. ears and kernels for cereal crops. In this manner, disruption of ABA perception or its signal transduction provides an effective strategy in insulating cereal female reproductive tissue growth from stress.

Environmental stresses following fertilization inhibit early events in establishment of sink capacity and can decrease yield. In cereals, for example, the endosperm is the major source of stored reserves within the mature seed. Storage capacity is established during an early stage of seed development. Recognizing ABA involvement in early plant responses to stress, the present invention is drawn to ablating the detrimental effects of ABA on the developing seed and improve the nature and quantity of seed and seed products, particularly cereals and grains. See, Mambelli and Setter (1998) *Physiologia Plantarum* 104:266-72 and Tuberosa et al. (1998) *Theor. Appl. Genet* 744-55.

As indicated, the invention comprises introducing sequences that modulate ABA perception and signal transduction into a target plant. By "sequences that modulate ABA perception and signal transduction" and "sequences involved in the perception and signal transduction of ABA" are intended mutants and genes that disrupt ABA synthesis or its perception and signal transduction. These mutants, genes, and sequences that disrupt ABA synthesis or its perception or signal transduction, are also called "ABA-associated sequences" herein. Such sequences include, but are not limited to, ABA-insensitive and hypersensitive mutants or antisense sequences corresponding to the mutant or wild-type genes. ABA mutants are known in the art and include abi1-5, era 1-3 (Cutler et al. (1996) *Science* 273:1239-41), gca1/8 (Benning et al. (1996) *Proc. Workshop Abscisic Acid Signal Transduction in Arabidopsis*, Madrid, p. 34), axr2 (Wilson et al. (1990) *Mol. Gen. Genet.* 222:377-83), jar1 (Staswick et al. (1992) *Proc. Natl. Acad. Sci. USA* 89:6837-40), jin4 (Berger et al. (1996) *Plant Physiol.* 111:525-31), bri1 (Clouse et al. (1996) *Plant Physiol.* 111:671-78), sax (*Arabidopsis thaliana*); vp1 (McCarty et al. (1991) *Cell* 66:895-905 and Robichaud et al. (1986) *J. Plant Physiol.* 126:235-42), and rea1 (Sturaro et al. (1996) *J. Exp. Bot.* 47:755-62) (*Zea mays*); cool (Raskin et al. (1988) *Planta* 173:73-78) (*Hordeum vulgare*); aba1 (Bitoun et al. (1990) Mol. Gen. Genet. 220:234-39 and Leydecker et al. (1995) *Plant Physiol.* 107:1427-31) (*Nicotiana plumbaginifolia*); and the like. These and other ABA-associated mutants can be used in the practice of the invention.

By "corresponding" to a gene or sequence is intended that the sequence is capable of hybridizing to the gene or sequence to the extent necessary to disrupt transcription. It is recognized that depending on the ABA-associated sequence utilized in the invention, the coding sequence or the antisense sequence may be preferred. However, the coding sequence may also be used to co-suppress expression of the target gene. For example, one strategy includes expression of mutant genes, such as abi1 or abi2 with an early kernel/embryo promoter to dominantly disrupt ABA action in tissues at early stages. Such an approach would not disrupt the later required ABA function in seed maturation. Alternatively, wild-type alleles of genes such as Vp1 may be down-regulated by co-suppression or antisense strategies to disrupt ABA action. In this latter example, an early kernel/embryo promoter may be used to drive expression of a coding sequence for Vp1(to co-suppress) or to drive expression of an antisense sequence for Vp1. A third example includes the transformation of a plant with a promoter for late period kernel development driving a wild-type Vp1 sequence. This transformed plant can then be crossed to a vp1 mutant plant. In this example, the inability of the vp1 mutant to be induced by ABA works to insulate early kernels from deleterious effects. At the same time, the DNA construct supplies kernels with the ability to mature normally. Thus, as described more fully below, several candidate gene targets are available to be coupled with promoters with limited expression patterns to provide increased yield stability in the face of abiotic stress.

The viviparous-1 (Vp1) gene of maize is required for expression of the maturation program in seed development. VP1 is a novel transcription factor possibly involved in potentiation of a seed-specific hormone response. The nucleic acid and amino acid sequence of Vp1 is in SEQ ID NOS: 1 and 2. The viviparous mutants of maize are blocked in the maturation program. As a result, the mutant embryo proceeds precociously into seedling development while attached to the mother plant. Several vivipary mutants have been identified. Further characteristics of a loss of function vp1 mutant include, for example, an ABA insensitive phenotype (i.e., a reduced sensitivity to germination inhibition by exogenous ABA in culture) and/or a decrease in Em promoter activation. It is well within skill in the art to identify loss of function mutations in Vp1 that are useful in the methods of the present invention. For example, Hill et al. ((1996) *Journal Biological Chemistry* 7:3366) have identified a role for the $NH^2$-terminal acidic region and the highly conserved BR1 domain of VP 1 as being essential for VP1 function. Other vp1 mutants are known. See, for example, Neill et al. (1986) *Planta* 169:87-96; McCarthy et al. (1991) *Cell* 66:895-905; Robichaud et al. (1980) *Dev. Genet.* 1:325-330; Robichaud and Sussex (1987) *Plant Physiol.* 130:181-188; Robichaud et al. (1986) *J. Plant Physiol.* 126:235-42; McCarthy et al. (1990) *Physiol. Plant* 81:267-72; and, Eyster et al. (1931) *Genetics* 16:457-590; all of which are herein incorporated by reference.

*Arabidopsis* ABA-insensitive, ABI, mutants are also available. Such mutants have pleiotropic defects in seed development, including decreased sensitivity to ABA inhibition of germination in altered seed-specific gene expression. See, Finkelstein et al. (1998) *The Plant Cell* 10:1043-1045; Leung et al. (1994) *Science* 264:1448-1452; Leung (1997) *Plant Cell* 9:759-771; Giraudat et al. (1992) *Plant Cell* 4:1251-1261; Myer et al. (1994) *Science* 264:1452-1455; Koornneef et al. (1989) *Plant Physiol.* 90:463-469; Nambara et al. (1992) *Plant J.* 2:435-441; Finkelstein and Somerville (1990) *Plant Physiol.* 94:1172-1179; Leung and Giraudat (1998) *Annu. Rev. Plant Physiol. Plant Mol. Biol.* 49:199-222; Robinson and Hill (1999) *Plant, Cell and Environment* 22:117-123; and Rodriguez et al. (1998) *FEBS Letters* 421:185-190, and the references cited therein, all of which are herein incorporated by reference. In addition, the nucleic acid and amino acid sequences of wild type ABI1, ABI2, ABI3, and ABI4 are set forth in SEQ ID NOS:3-10. Other ABA-associated mutants include bri1 from *Arabidopsis thaliana* the sequence of which can be found in Genbank Accession No. AF017056 and Li et al. (1997) Cell 90:929-938, both of which are herein incorporated by reference.

An abi mutant of interest includes, for example, abi1. abi1 is a dominant mutation in the structural part of the ABI1 gene. The mutation has been characterized and comprises a nucleotide base transition from guanine to adenine and changes the DNA sequence GGC to GAC, thus causing the wild type glycine residue at amino acid position 180 of SEQ ID NO:3 to be replaced with aspartic acid (Meyer et al. (1994) *Science* 264:1452-1455). abi2 is another dominant mutation of interest in the methods of the invention. abi2 is characterized by a GGC to GAC transition leading to the replacement the Gly residue at amino acid position 168 of SEQ ID NO:6 to Asp (Rodriquez et al. (1998) *FEBS Letters* 421:18-190). It is well within skill in the art to identify other mutations (both dominant and recessive) in other ABA-associated sequences that will be useful in the methods of the present invention.

Such mutants listed above are designated "ABA-associated mutants." By "ABA-associated mutants" is intended genes and sequences which disrupt ABA signaling and/or perception in a plant. Utilizing the sequences above, related sequences from other plants, including cereals, can be isolated. In some instances, it may be beneficial to use the ABA-associated sequence that corresponds with a sequence from the target plant of interest. For example, for use in maize, the maize homolog of the ABA-associated sequence, or a sequence corresponding to the maize homolog, may be preferred.

The invention utilizes the ABA-associated sequences to control the plant response to ABA. Generally, it will be beneficial to block ABA signaling or perception to prevent a loss of yield. Utilizing the ABA-associated sequences, coding sequences, and antisense sequences, the expression and perception of ABA in a plant can be controlled. As described in more detail below, such sequences can be introduced into plants of interest by recombinant methods as well as by traditional breeding methods.

The nucleotide sequences of the invention can be used to isolate corresponding sequences from other organisms, particularly other plants more particularly cereals. In this manner, methods such as PCR, hybridization, and the like can be used to identify such sequences based on their sequence homology to the ABA-associated sequences known in the art. Sequences may be isolated based on their sequence identity to the entire ABA-associated sequence or to fragments thereof.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen plant. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the ABA-associated sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, an entire ABA-associated sequence, or one or more portions thereof, may be used as a probe capable of specifically hybridizing to corresponding sequences and messenger RNAs. To achieve specific hybridization under a variety of conditions, such probes include sequences that are unique among the sequences of interest and are preferably at least about 10 nucleotides in length, and most preferably at least about 20 nucleotides in length. Such probes may be used to amplify corresponding sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Duration of hybridization is generally less than about 24 hours, usually about 4 to 12. Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated "corresponding ABA-associated sequences" that modulate the plant response to ABA and which hybridize under stringent conditions to the ABA-associated sequences disclosed herein, or to fragments thereof, are encompassed by the present invention. Such sequences will be at least about 40% to 50% homologous, about 60%, 65%, or 70% homologous, and even at least about 75%, 80%, 85%, 90%, 91%, 92%, 93%, 94%, 95%, 96%, 97%, 98%, 99% or more homologous with the disclosed sequences. That is, the sequence identity of sequences may range, sharing at least about 40% to 50%, about 60%, 65%, or 70%, and even at least about 75%, 80%, 85%, 90%, 91%, 92%, 93%, 94%, 95%, 96%, 97%, 98%, 99% or more sequence identity.

The ABA-associated sequences of the invention can be utilized with tissue or developmental-specific promoters to disrupt ABA function in a tissue or a developmentally specific manner. Promoters of particular interest include seed-preferred promoters, particularly early kernel/embryo promoters and late kernel/embryo promoters.

Kernel development post-pollination is divided into approximately three primary phases. The lag phase of kernel growth occurs from about 0 to 10-12 days after pollination. During this phase the kernel is not growing significantly in mass, but rather important events are being carried out that will determine kernel vitality (i.e., number of cells). The linear grain fill stage occurs from about 10-12 to about 40 DAP. During this stage of kernel development, the kernel attains almost all of its final mass and various storage products (i.e., starch, protein, oil) are produced. Finally, the maturation phase occurs from about 40 DAP to harvest. During this phase of kernel development the kernel becomes quiescent and begins to dry down in preparation for a long period of dormancy prior to germination. As defined herein "Early kernel/embryo promoters" are promoters that are on during the first phase of development (i.e., from about 0 to about 12 DAP). "Late kernel/embryo promoters", as defined herein, are on from about 12 DAP through maturation. The choice of the promoter will depend on the ABA associated sequence utilized.

Early kernel/embryo promoters include, for example, cim1, a pollen and whole kernel specific promoter that is active 5 DAP. See, for example, WO 00/11177, which is herein incorporated by reference. Other early kernel/embryo promoters include the seed-preferred promoters end1, which is active 7-10 DAP, and end2, which is active 9-14 DAP in the whole kernel and active 10 DAP in the endosperm and pericarp. See, for example, WO 00/12733, herein incorporated by reference. Additional early kernel/embryo promoters that find use in the methods of the present invention include the seed-preferred promoter lpt2 (SEQ ID NO:13) which is active 6 to 24 DAP (U.S. Pat. No. 5,525,716, herein incorporated by reference).

Such early kernel/embryo promoters can be used with genes or mutants in the perception/signal transduction pathway for ABA. In this manner, mutant genes such as abi1 or abi2 operably linked to an early kernel/embryo promoter would dominantly disrupt ABA action in tissues prior to the later required ABA function in seed maturation. Alternatively, an early kernel/embryo promoter can be operably linked to a wild type (co suppression) or antisence nucleotide sequence of an ABA associated sequence. The early kernel/embryo promoter would be utilized to disrupt ABA action in tissues prior to seed maturation.

Late kernel/embryo promoters include, for example, promoters from oleosin genes. See, for example, Plant et al. (1994) *Plant Mol. Biol.* 25:193-205; Keddie et al. (1994) *Plant Mol. Biol.* 24:327-40; Keddie et al. (1992) *Plant Mol. Biol.* 19:443-53; and Hong et al. (1997) 34:549-55; herein incorporated by reference. See also, Genbank Accession Nos. U71381 (SEQ ID NO:11), AF134411 (SEQ ID NO:12), and U.S. Pat. No. 5,977,436, which contain oleosin promoter sequences from *Glycine max, Brassica juncea*, and *Arabidopsis thaliana*, respectively. All of these references are herein incorporated by reference. Additional late kernel/embryo promoters include, smilps, an embryo specific promoter that is active 13-14 DAP and cz19B1a whole kernel specific promoter that is active 13-40 DAP. See, for example, WO 00/11177, which is herein incorporated by reference. The seed-preferred promoter a13 is active 24-40 days after flowering and may also be used in the methods of the invention. See, for example, WO 00/40710, which is herein incorporated by reference.

Late kernel/promoters, such as those from oleosin genes, can be used to drive expression of a wild-type Vp1 allele. Such plants can then be crossed to a plant having a vp1 mutant. In this example, the inability of the vp1 mutant allele to be complemented by ABA would insulate early kernels from deleterious effects. The Vp1 gene product is on very early in kernel development. In the presence of ABA, the VP1 becomes effective. The engineered gene supplied by the transgenic parent would supply the kernels with the ability to mature normally. As used herein, an "endogenous ABA associated sequence" is defined as any ABA associated sequence not introduced into the plant via a transformation event.

Such ABA-associated genes can be utilized to control the effects of stress on the plant. Since the accumulation of nutritive reserves in the acquisition of desiccation tolerance are associated with the expression of specific sets of mRNAs. Transcripts encoding either storage proteins or late-embryogenesis-abundant (LEA) proteins thought to participate in desiccation tolerance can be precociously induced by exogenous ABA in cultured embryos. Thus, late expression of ABA genes can be coupled with transgenic seed storage proteins to increase nutritive reserves in seeds.

By "introducing" sequences that modulate ABA perception and signal transduction into a target plant encompasses any means for incorporating the sequence of interest into the target plant. Such means includes conventional breeding methods, genetic transformation methods, or other such means as may be available. The methods of the invention do not depend on a particular method for introducing a nucleotide construct to a plant, only that the nucleotide construct gains access to the interior of at least one cell of the plant. By "stable transformation" is intended that the nucleotide construct introduced into a plant integrates into the genome of the plant and is capable of being inherited by progeny thereof.

Wild-type alleles of genes such as Vp1 may be down-regulated with early promoters via either cosuppression or antisense strategies. It is recognized that with these nucleotide sequences, antisense constructions complementary to at least a portion of the messenger RNA (mRNA) for the ABA-associated sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence similarity to the corresponding anti-sensed sequences may be used. Furthermore, portions of the antisense nucleotides may be used to disrupt the expression of the target gene. Generally, sequences of at least 50 nucleotides, 100 nucleotides, 200 nucleotides, or greater may be used.

Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene (i.e, an ABA-associated sequence). Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

It is recognized that fragments and/or variants of the ABA-associated genes can be utilized in the invention. Fragments and variants of the ABA-associated nucleotide sequences and proteins encoded thereby are thus encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence act to modulate responses to ABA. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence of the invention.

By "variants" is intended substantially similar sequences. For nucleotide sequences naturally occurring variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis. Generally, variants of a particular nucleotide sequence of the invention will have at least about 40%, 50%, 60%, 65%, 70%, generally at least about 75%, 80%, 85%, preferably at least about 90%, 92%, 94%, 95%, 96%, 97%, and more preferably at least about 98%, 99% or more sequence identity to that particular nucleotide sequence as determined by sequence alignment programs described elsewhere herein using default parameters.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) *CABIOS* 4:11-17; the local homology algorithm of Smith et al. (1981) *Adv. Appl. Math.* 2:482; the homology alignment algorithm of Needleman and Wunsch (1970) *J. Mol. Biol.* 48:443-453; the search-for-similarity-method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See the website at ncbi.nlm.nih.gov. Alignment may also be performed manually by inspection.

Unless otherwise stated, sequence identity/similarity values provided herein refer to the value obtained using GAP Version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

GAP uses the algorithm of Needleman and Wunsch (1970) *J. Mol. Biol.* 48: 443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation.

The proteins of the invention may be altered in various ways including amino acid substitutions, deletions, truncations, and insertions. Methods for such manipulations are generally known in the art. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154: 367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays.

Variant nucleotide sequences and proteins also encompass sequences and proteins derived from a mutagenic and recombinogenic procedure such as DNA shuffling. With such a procedure, one or more different ABA-associated coding sequences can be manipulated to create a new ABA-associated protein possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The ABA-associated sequences of the invention are provided in expression cassettes for expression in the plant of interest. The cassette will include 5' and 3' regulatory sequences operably linked to an ABA-associated sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the sequence of interest to be under the transcriptional regulation of the regulatory regions. The expression cassette may additionally contain selectable marker genes.

The expression cassette will include in the 5'-3' direction of transcription, a transcriptional and translational initiation region, a DNA sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence. While it may be preferable to express the sequences using heterologous promoters, the native promoter sequences may be used. Thus, the phenotype of the plant or plant cell is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed plant. That is, the genes can be synthesized using plant-preferred codons for improved expression. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS USA* 86:6126-6130); potyvirus leaders, for example, TEV leader (Tobacco Etch Virus) (Allison et al. (1986); MDMV leader (Maize Dwarf Mosaic Virus); *Virology* 154:9-20), and human immunoglobulin heavy-chain binding protein (BiP), (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (Townsend et al., U.S. Pat. No. 5,563,055; U.S. Pat. No. 5,981,840), direct gene transfer (Paszkowski et al. (1984) *EMBO J.* 3:2717-2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923-926). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) In Vitro *Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322, 783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

The present invention may be used for transformation of any plant species, including, but not limited to, monocots and dicots. Examples of plants of interest include, but are not limited to, corn (*Zea mays*), Brassica sp. (e.g., *B. napus, B. rapa, B. juncea*), particularly those Brassica species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g. *Lactuca sativa*), green beans (*Phaseolus vulgaris*), lima beans (*Phaseolus limensis*), peas (*Lathyrus* spp.), and members of the genus Cucumis such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbiapulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, Brassica, soybean, cotton, safflower, peanut, sorghum, wheat, millet, tobacco, etc.), more preferably corn and soybean plants, yet more preferably corn plants.

Plants of particular interest include grain plants that provide seeds of interest, oil-seed plants, and leguminous plants. Seeds of interest include grain seeds, such as corn, wheat, barley, rice, sorghum, rye, etc. Oil seed plants include cotton, soybean, safflower, sunflower, Brassica, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

The following examples are offered by way of illustration and not by way of limitation.

EXPERIMENTAL

Transformation and Regeneration of Transgenic Plants

Example 1

Transformation and Regeneration of Transgenic Maize Plants

Immature maize embryos from greenhouse donor plants are bombarded with a plasmid containing the ABI3 sequence operably linked to an early kernel/embryo promoter plus a plasmid containing the selectable marker gene PAT (Wohlleben et al. (1988) *Gene* 70:25-37) that confers resistance to the herbicide Bialaphos. Transformation is performed as follows. All media recipes are below.

Preparation of Target Tissue

The ears are surface sterilized in 30% Chlorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the ABI3 sequence operably linked to an early kernel/embryo promoter is made. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water
10 μl (1 μg) DNA in TrisEDTA buffer (1 μg total)
100 μl 2.5 M $CaCl_2$
10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored.

Bombardment and Culture Media

Bombardment medium (560Y) comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I H$_2$O); and 0.85 mg/l silver nitrate and 3.0 mg/l bialaphos(both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I H$_2$O) (Murashige and Skoog (1962) Physiol. Plant. 15:473), 100 mg/l myo-inositol, 0.5 mg/l zeatin, 60 g/l sucrose, and 1.0 ml/l of 0.1 mM abscisic acid (brought to volume with polished D-I H$_2$O after adjusting to pH 5.6); 3.0 g/l Gelrite (added after bringing to volume with D-I H$_2$O); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I H$_2$O), 0.1 g/l myo-inositol, and 40.0 g/l sucrose (brought to volume with polished D-I H$_2$O after adjusting pH to 5.6); and 6 g/l bacto-agar (added after bringing to volume with polished D-I H$_2$O), sterilized and cooled to 60° C.

Example 2

*Agrobacterium*-Mediated Transformation

For *Agrobacterium*-mediated transformation of maize with an ABI3 sequence operably linked to an early kernel/embryo promoter, preferably the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring the ABI3 sequence operably linked to an early kernel/embryo promoter to at least one cell of at least one of the immature embryos (step 1: the infection step). In this step the immature embryos are preferably immersed in an *Agrobacterium* suspension for the initiation of inoculation. The embryos are co-cultured for a time with the *Agrobacterium* (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

Example 3

Soybean Embryo Transformation

Soybean embryos are bombarded with a plasmid containing the ABI3 nucleotide sequence operably linked to an early embryo/kernel promoter as follows. To induce somatic embryos, cotyledons, 3-5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature* (London) 327:70-73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the $^{35}$S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188), and the 3' region of the nopaline synthase gene from the T-DNA of the Ti plasmid of *Agrobacterium tumefaciens*. The expression cassette comprising the ABI3 nucleotide sequence operably linked to an early kernel/embryo promoter can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl CaCl$_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 4

Sunflower Meristem Tissue Transformation

Sunflower meristem tissues are transformed with an expression cassette containing the ABI3 sequence operably linked to an early kernel embryo promoter as follows (see also European Patent Number EP 0 486233, herein incorporated by reference, and Malone-Schoneberg et al. (1994) *Plant Science* 103:199-207). Mature sunflower seed (*Helianthus annuus* L.) are dehulled using a single wheat-head thresher. Seeds are surface sterilized for 30 minutes in a 20% Clorox bleach solution with the addition of two drops of Tween 20 per 50 ml of solution. The seeds are rinsed twice with sterile distilled water.

Split embryonic axis explants are prepared by a modification of procedures described by Schrammeijer et al. (Schrammeijer et al. (1990) *Plant Cell Rep.* 9: 55-60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige et al. (1962) *Physiol. Plant.*, 15: 473-497), Shepard's vitamin additions (Shepard (1980) in *Emergent Techniques for the Genetic Improvement of Crops* (University of Minnesota Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid ($GA_3$), pH 5.6, and 8 g/l Phytagar.

The explants are subjected to microprojectile bombardment prior to *Agrobacterium* treatment (Bidney et al. (1992) *Plant Mol. Biol.* 18: 301-313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the ABI3 gene operably linked to an early kernel/embryo promoter is introduced into *Agrobacterium* strain EHA105 via freeze-thawing as described by Holsters et al. (1978) *Mol. Gen. Genet.* 163:181-187. This plasmid further comprises a kanamycin selectable marker gene (i.e, nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an $OD_{600}$ of about 0.4 to 0.8. The *Agrobacterium* cells are pelleted and resuspended at a final $OD_{600}$ of 0.5 in an inoculation medium comprised of 12.5 mM MES pH 5.7, 1 gm/l $NH_4Cl$, and 0.3 gm/l $MgSO_4$.

Freshly bombarded explants are placed in an *Agrobacterium* suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for a modulation in the plant response to ABA.

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by, for example, NPTII ELISA of leaf extracts while transgenic seeds harvested from NPTII-positive $T_0$ plants are identified by assaying for a modulation in the plant response to ABA.

Example 5

Transgenic maize plants are generated by the methods of example 1 using a DNA construction comprising a wild type Vp1 sequence (SEQ ID NO:1) operably linked to the oleosin promoter. The plasmid further contains the selectable marker PAT (Wohlleben et al. (1998) Gene 70:25-37). As described in Example 1, plants having stably incorporated the oleosin:Vp1 DNA construct are isolated.

Maize plants having a loss of function mutation in vp1 are isolated as described in Eyster et al. (1931) *Genetics* 16:574-590, herein incorporated by reference. Such plants are characterized as having a reduced sensitivity to ABA. Transgenic maize plants having stably incorporated the oleosin:Vp1 DNA construct are crossed to the maize plant having the vp1 loss of function mutation. The resulting progeny are back-crossed to produce a plant having the following genotype: vp1/vp1; oleosin:Vp1/oleosin:Vp1. This plant will be insulated from the deleterious effects of ABA in the early embryo and will be supplied with VP1 in late kernel/embryo development, allowing kernels to mature normally.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for increasing yield in a maize plant under an abiotic environmental stress said method comprising the steps of:
   (a) transforming stably maize plant cells with a DNA construct which comprises a nucleotide sequence encoding a polypeptide having at least 95% amino acid sequence identity to the amino acid sequence as set forth in SEQ ID NO:4, wherein the nucleotide sequence is operably linked to an early kernel/embryo promoter that is active during the first phase of seed development, wherein the first phase of seed development is from 0 to about 12 days after pollination (DAP), wherein said early kernel/embryo promoter is heterologous to said nucleotide sequence, and wherein said early kernel/embryo promoter is inactive in the embryo during the maturation phase of seed development;
   (b) regenerating transgenic maize plants from the transformed maize plant cells of step (a);
   (c) growing the transformed maize plants of step (b) under an abiotic environmental stress, and expressing said polypeptide during the early phase of maize kernel/embryo development to reduce sensitivity to abscisic acid (ABA) during said early phase of maize kernel/embryo development, wherein said kernel/embryo is being produced on said transformed maize plant, thereby reducing the detrimental effects of said stress on the developing maize plant seed; and
   (d) harvesting mature seeds from the transformed maize plants of step (c) to determine yield, whereby said method results in an increased yield as compared to a maize plant lacking said DNA construct.

2. The method of claim 1, wherein said polypeptide has the amino acid sequence as set forth in SEQ ID NO: 4.

3. The method of claim 1, wherein said nucleotide sequence has at least 95% sequence identity to the nucleotide sequence as set forth in SEQ ID NO: 3.

4. The method of claim 1, wherein said nucleotide sequence is set forth in SEQ ID NO: 3.

* * * * *

SEQUENCE LISTING

<160> NUMBER OF SEQ ID NOS: 13

<210> SEQ ID NO 1
<211> LENGTH: 2456
<212> TYPE: DNA
<213> ORGANISM: Zea mays
<220> FEATURE:
<221> NAME/KEY: misc_feature
<222> LOCATION: (0)...(0)
<223> OTHER INFORMATION: vp1 cDNA (Genbank Accession No. M60214)
<220> FEATURE:
<221> NAME/KEY: CDS
<222> LOCATION: (73)...(2148)

<400> SEQUENCE: 1

```
ctacacccga gaggcggcgg cggcagacac agacaccgtc tctctcctcc ctttgtcgtc      60
gtgcctctct gc atg gaa gcc tcc tcc ggc tcg tcg cca ccg cac tcc caa     111
              Met Glu Ala Ser Ser Gly Ser Ser Pro Pro His Ser Gln
                1               5                  10 gag aac ccg ccg gag cac ggt ggc gac atg gga ggg gcc ccc gcg gag        159
Glu Asn Pro Pro Glu His Gly Gly Asp Met Gly Gly Ala Pro Ala Glu
 15              20                  25 gag atc gga ggg gag gcg gcg gat gac ttc atg ttc gct gaa gac acg        207
Glu Ile Gly Gly Glu Ala Ala Asp Asp Phe Met Phe Ala Glu Asp Thr
30              35                  40                  45 ttc ccc tcc ctc ccg gac ttc cct tgc ctt tcg tcg ccg tcc agc tcc        255
Phe Pro Ser Leu Pro Asp Phe Pro Cys Leu Ser Ser Pro Ser Ser Ser
                50                  55                  60 acc ttc tcg tcc aac tcc tcg tca aac tcc tcc agc gcc tac acc aac        303
Thr Phe Ser Ser Asn Ser Ser Ser Asn Ser Ser Ser Ala Tyr Thr Asn
             65                  70                  75 acg gca gga aga gcc ggc ggc gag ccc tcc gag cct gct tcg gcc gga        351
Thr Ala Gly Arg Ala Gly Gly Glu Pro Ser Glu Pro Ala Ser Ala Gly
         80                  85                  90 gaa ggg ttt gat gcg ctc gat gac atc gac cag ctc ctc gac ttc gcg        399
Glu Gly Phe Asp Ala Leu Asp Asp Ile Asp Gln Leu Leu Asp Phe Ala
     95                 100                 105 tcg ctt tcc atg ccg tgg gac tcc gag ccg ttc ccg ggg gtt agc atg        447
Ser Leu Ser Met Pro Trp Asp Ser Glu Pro Phe Pro Gly Val Ser Met
110                 115                 120                 125 atg cta gag aac gcc atg tcg gcg ccg ccg cag ccg gtg ggc gac ggc        495
Met Leu Glu Asn Ala Met Ser Ala Pro Pro Gln Pro Val Gly Asp Gly
                130                 135                 140 atg agt gaa gag aaa gcc gtg ccg gaa ggg acc acg ggg gga gag gag        543
Met Ser Glu Glu Lys Ala Val Pro Glu Gly Thr Thr Gly Gly Glu Glu
            145                 150                 155 gcc tgc atg gat gcg tcg gag ggg gag gag ctg ccg cgg ttc ttc atg        591
Ala Cys Met Asp Ala Ser Glu Gly Glu Glu Leu Pro Arg Phe Phe Met
        160                 165                 170 gag tgg ctc acg agc aac cgc gaa aac atc tcg gcc gag gat ctc cgc        639
Glu Trp Leu Thr Ser Asn Arg Glu Asn Ile Ser Ala Glu Asp Leu Arg
    175                 180                 185 ggg atc cgc ctc cgc cgc tcc acc atc gag gcc gcc gcc gcc cgg ctc        687
Gly Ile Arg Leu Arg Arg Ser Thr Ile Glu Ala Ala Ala Ala Arg Leu
190                 195                 200                 205 ggc ggc ggg cgc cag ggc acc atg cag ctg ctc aag ctc atc ctc acc        735
Gly Gly Gly Arg Gln Gly Thr Met Gln Leu Leu Lys Leu Ile Leu Thr
                210                 215                 220 tgg gtg cag aac cac cac ctc cag agg aag cgc ccg cgc gac gtg atg        783
Trp Val Gln Asn His His Leu Gln Arg Lys Arg Pro Arg Asp Val Met
            225                 230                 235
```

-continued

| | |
|---|---|
| gag gag gag gcg ggc ctg cac gtc cag ctc ccc agc ccg gtc gcc aac<br>Glu Glu Glu Ala Gly Leu His Val Gln Leu Pro Ser Pro Val Ala Asn<br>     240                           245                            250 | 831 |
| cca cca gga tac gag ttc ccc gcc ggc gga cag gac atg gcc gcg ggc<br>Pro Pro Gly Tyr Glu Phe Pro Ala Gly Gly Gln Asp Met Ala Ala Gly<br>255                          260                         265 | 879 |
| ggc ggc aca tct tgg atg ccc cac cag cag gca ttc acg ccg cct gct<br>Gly Gly Thr Ser Trp Met Pro His Gln Gln Ala Phe Thr Pro Pro Ala<br>270                         275                         280                  285 | 927 |
| gcg tac ggc ggc gac gcg gtg tac ccg agc gcg gca ggc caa cag tac<br>Ala Tyr Gly Gly Asp Ala Val Tyr Pro Ser Ala Ala Gly Gln Gln Tyr<br>                 290                        295                         300 | 975 |
| tct ttc cac cag ggc ccc agc acg agc agc gtg gtc gtg aac agc caa<br>Ser Phe His Gln Gly Pro Ser Thr Ser Ser Val Val Val Asn Ser Gln<br>     305                           310                         315 | 1023 |
| ccg ttc tcc ccg ccg cct gtg ggc gac atg cac ggc gcg aac atg gcc<br>Pro Phe Ser Pro Pro Pro Val Gly Asp Met His Gly Ala Asn Met Ala<br>320                         325                         330 | 1071 |
| tgg ccg cag cag tac gtg ccg ttc cca ccg cct ggg gct tcc acg ggc<br>Trp Pro Gln Gln Tyr Val Pro Phe Pro Pro Pro Gly Ala Ser Thr Gly<br>     335                           340                         345 | 1119 |
| tct tac cct atg ccg cag ccg ttc tcc ccc gga ttc ggc ggg cag tac<br>Ser Tyr Pro Met Pro Gln Pro Phe Ser Pro Gly Phe Gly Gly Gln Tyr<br>350                         355                         360                  365 | 1167 |
| gcc ggc gcc ggc gct ggc cac ctc tca gtg gcc ccc cag cgc atg gca<br>Ala Gly Ala Gly Ala Gly His Leu Ser Val Ala Pro Gln Arg Met Ala<br>                 370                        375                         380 | 1215 |
| ggc gtg gag gcc tcg gcg acc aag gag gcc cgc aag aag cgc atg gcg<br>Gly Val Glu Ala Ser Ala Thr Lys Glu Ala Arg Lys Lys Arg Met Ala<br>     385                           390                         395 | 1263 |
| aga cag cgg cgc ctg tcc tgc ctg cag cag cag cgc agc cag cag ctg<br>Arg Gln Arg Arg Leu Ser Cys Leu Gln Gln Gln Arg Ser Gln Gln Leu<br>400                         405                         410 | 1311 |
| agc ctg ggc cag atc cag acc tcc gtc cac ctg cag gag ccg tcc cct<br>Ser Leu Gly Gln Ile Gln Thr Ser Val His Leu Gln Glu Pro Ser Pro<br>     415                           420                         425 | 1359 |
| cgg tcc acg cac tcc ggc ccg gtc acg ccg tca gca ggc ggc tgg gga<br>Arg Ser Thr His Ser Gly Pro Val Thr Pro Ser Ala Gly Gly Trp Gly<br>430                         435                         440                  445 | 1407 |
| ttc tgg tcg ccg agc agc cag cag cag gtc cag aac ccg ctc tcc aag<br>Phe Trp Ser Pro Ser Ser Gln Gln Gln Val Gln Asn Pro Leu Ser Lys<br>                 450                        455                       460 | 1455 |
| tcc aat tcc tca agg gcg ccg cct tcc tcg ctg gaa gcg gcg gcg gcg<br>Ser Asn Ser Ser Arg Ala Pro Pro Ser Ser Leu Glu Ala Ala Ala Ala<br>                 465                        470                       475 | 1503 |
| gct cca cag aca aag ccc gcg cct gct ggt gct cgg cag gac gac att<br>Ala Pro Gln Thr Lys Pro Ala Pro Ala Gly Ala Arg Gln Asp Asp Ile<br>480                         485                         490 | 1551 |
| cac cac cgc ctc gca gcg gct tca gat aag cgg cag ggc gcc aag gcg<br>His His Arg Leu Ala Ala Ala Ser Asp Lys Arg Gln Gly Ala Lys Ala<br>     495                           500                         505 | 1599 |
| gac aag aac ctg cgg ttc ctg ctg cag aag gtg ctg aag cag agc gac<br>Asp Lys Asn Leu Arg Phe Leu Leu Gln Lys Val Leu Lys Gln Ser Asp<br>510                         515                         520                  525 | 1647 |
| gtc ggg agc ctc ggc cgc atc gtg ctc ccc aaa aag gaa gcg gag gtt<br>Val Gly Ser Leu Gly Arg Ile Val Leu Pro Lys Lys Glu Ala Glu Val<br>                 530                        535                         540 | 1695 |
| cac ctg ccg gag ctg aag acg agg gat ggc atc tcc atc ccc atg gag<br>His Leu Pro Glu Leu Lys Thr Arg Asp Gly Ile Ser Ile Pro Met Glu<br>     545                           550                         555 | 1743 |

-continued

```
gac atc gga acg tcg cgc gtg tgg aac atg cgg tac agg ttt tgg ccc      1791
Asp Ile Gly Thr Ser Arg Val Trp Asn Met Arg Tyr Arg Phe Trp Pro
        560                 565                 570 aac aac aag agc aga atg tat ctg ctg gaa aac aca ggg gaa ttt gtt      1839
Asn Asn Lys Ser Arg Met Tyr Leu Leu Glu Asn Thr Gly Glu Phe Val
575                 580                 585 cgt tcc aac gag ctt cag gag ggg gat ttc ata gtg atc tac tcc gat      1887
Arg Ser Asn Glu Leu Gln Glu Gly Asp Phe Ile Val Ile Tyr Ser Asp
590                 595                 600                 605 gtc aag tcg ggc aaa tat ctg ata cgg ggc gtg aag gta agg ccc ccg      1935
Val Lys Ser Gly Lys Tyr Leu Ile Arg Gly Val Lys Val Arg Pro Pro
                610                 615                 620 ccg gcg caa gag caa ggc agt ggt tcc agc ggg gga ggc aag cac agg      1983
Pro Ala Gln Glu Gln Gly Ser Gly Ser Ser Gly Gly Gly Lys His Arg
            625                 630                 635 ccc ctc tgt cca gca ggt cca gag aga gcc gca gcc gcc ggt gct cct      2031
Pro Leu Cys Pro Ala Gly Pro Glu Arg Ala Ala Ala Ala Gly Ala Pro
        640                 645                 650 gaa gac gcc gtc gtc gac ggg gtc agc ggc gcc tgc aag ggg agg tct      2079
Glu Asp Ala Val Val Asp Gly Val Ser Gly Ala Cys Lys Gly Arg Ser
655                 660                 665 ccg gaa ggc gtg cgg cgg gtt cgg cag cag gga gcc ggc gcc atg agc      2127
Pro Glu Gly Val Arg Arg Val Arg Gln Gln Gly Ala Gly Ala Met Ser
670                 675                 680                 685 cag atg gcg gtg agc atc tga aagagcagca ggctccgcca tatattgatc         2178
Gln Met Ala Val Ser Ile
                690 gatcgaccaa tcgatcgtta gttctccaag ttactattag ctagctatag cccgaaacag   2238 ctgaactgat gatgacgatg gtaacctccg tcgtgtgtgt gctaagcatg tagcgtgcta   2298 ggagatgata tattaaatat aatcgagtag tagagcctac ccgctgtgtg acgctaaatt   2358 tgtgtgcatt tggtttggtt tgtgagttgg gcccgtgcgt ggctgtgtca tgtcgtggtt   2418 aattagctat actagtcctg tctgtacatg catggaca                           2456

<210> SEQ ID NO 2
<211> LENGTH: 691
<212> TYPE: PRT
<213> ORGANISM: Zea mays

<400> SEQUENCE: 2

Met Glu Ala Ser Ser Gly Ser Ser Pro Pro His Ser Gln Glu Asn Pro
1               5                   10                  15

Pro Glu His Gly Gly Asp Met Gly Gly Ala Pro Ala Glu Glu Ile Gly
            20                  25                  30

Gly Glu Ala Ala Asp Asp Phe Met Phe Ala Glu Asp Thr Phe Pro Ser
        35                  40                  45

Leu Pro Asp Phe Pro Cys Leu Ser Ser Pro Ser Ser Thr Phe Ser
    50                  55                  60

Ser Asn Ser Ser Asn Ser Ser Ala Tyr Thr Asn Thr Ala Gly
65                  70                  75                  80

Arg Ala Gly Gly Glu Pro Ser Glu Pro Ala Ser Ala Gly Glu Gly Phe
                85                  90                  95

Asp Ala Leu Asp Asp Ile Asp Gln Leu Leu Asp Phe Ala Ser Leu Ser
            100                 105                 110

Met Pro Trp Asp Ser Glu Pro Phe Pro Gly Val Ser Met Met Leu Glu
        115                 120                 125

Asn Ala Met Ser Ala Pro Pro Gln Pro Val Gly Asp Gly Met Ser Glu
```

-continued

```
            130                 135                 140
Glu Lys Ala Val Pro Glu Gly Thr Thr Gly Glu Ala Cys Met
145                 150                 155                 160

Asp Ala Ser Glu Gly Glu Leu Pro Arg Phe Phe Met Glu Trp Leu
                165                 170                 175

Thr Ser Asn Arg Glu Asn Ile Ser Ala Glu Asp Leu Arg Gly Ile Arg
            180                 185                 190

Leu Arg Arg Ser Thr Ile Glu Ala Ala Ala Arg Leu Gly Gly Gly
                195                 200                 205

Arg Gln Gly Thr Met Gln Leu Leu Lys Leu Ile Leu Thr Trp Val Gln
210                 215                 220

Asn His His Leu Gln Arg Lys Arg Pro Arg Asp Val Met Glu Glu Glu
225                 230                 235                 240

Ala Gly Leu His Val Gln Leu Pro Ser Pro Val Ala Asn Pro Pro Gly
                245                 250                 255

Tyr Glu Phe Pro Ala Gly Gly Gln Asp Met Ala Gly Gly Gly Thr
                260                 265                 270

Ser Trp Met Pro His Gln Gln Ala Phe Thr Pro Pro Ala Ala Tyr Gly
            275                 280                 285

Gly Asp Ala Val Tyr Pro Ser Ala Ala Gly Gln Gln Tyr Ser Phe His
290                 295                 300

Gln Gly Pro Ser Thr Ser Val Val Val Asn Ser Gln Pro Phe Ser
305                 310                 315                 320

Pro Pro Pro Val Gly Asp Met His Gly Ala Asn Met Ala Trp Pro Gln
                325                 330                 335

Gln Tyr Val Pro Phe Pro Pro Gly Ala Ser Thr Gly Ser Tyr Pro
                340                 345                 350

Met Pro Gln Pro Phe Ser Pro Gly Phe Gly Gln Tyr Ala Gly Ala
            355                 360                 365

Gly Ala Gly His Leu Ser Val Ala Pro Gln Arg Met Ala Gly Val Glu
370                 375                 380

Ala Ser Ala Thr Lys Glu Ala Arg Lys Lys Arg Met Ala Arg Gln Arg
385                 390                 395                 400

Arg Leu Ser Cys Leu Gln Gln Arg Ser Gln Gln Leu Ser Leu Gly
                405                 410                 415

Gln Ile Gln Thr Ser Val His Leu Gln Glu Pro Ser Pro Arg Ser Thr
            420                 425                 430

His Ser Gly Pro Val Thr Pro Ser Ala Gly Gly Trp Gly Phe Trp Ser
                435                 440                 445

Pro Ser Ser Gln Gln Gln Val Gln Asn Pro Leu Ser Lys Ser Asn Ser
450                 455                 460

Ser Arg Ala Pro Pro Ser Ser Leu Glu Ala Ala Ala Ala Pro Gln
465                 470                 475                 480

Thr Lys Pro Ala Pro Ala Gly Ala Arg Gln Asp Ile His His Arg
                485                 490                 495

Leu Ala Ala Ala Ser Asp Lys Arg Gln Gly Ala Lys Ala Asp Lys Asn
                500                 505                 510

Leu Arg Phe Leu Leu Gln Lys Val Leu Lys Gln Ser Asp Val Gly Ser
            515                 520                 525

Leu Gly Arg Ile Val Leu Pro Lys Lys Glu Ala Glu Val His Leu Pro
530                 535                 540

Glu Leu Lys Thr Arg Asp Gly Ile Ser Ile Pro Met Glu Asp Ile Gly
545                 550                 555                 560
```

```
Thr Ser Arg Val Trp Asn Met Arg Tyr Arg Phe Trp Pro Asn Asn Lys
            565                 570                 575

Ser Arg Met Tyr Leu Leu Glu Asn Thr Gly Glu Phe Val Arg Ser Asn
        580                 585                 590

Glu Leu Gln Glu Gly Asp Phe Ile Val Ile Tyr Ser Asp Val Lys Ser
        595                 600                 605

Gly Lys Tyr Leu Ile Arg Gly Val Lys Val Arg Pro Pro Ala Gln
        610                 615                 620

Glu Gln Gly Ser Gly Ser Ser Gly Gly Lys His Arg Pro Leu Cys
625                 630                 635                 640

Pro Ala Gly Pro Glu Arg Ala Ala Ala Gly Ala Pro Glu Asp Ala
                645                 650                 655

Val Val Asp Gly Val Ser Gly Ala Cys Lys Gly Arg Ser Pro Glu Gly
                660                 665                 670

Val Arg Arg Val Arg Gln Gln Gly Ala Gly Ala Met Ser Gln Met Ala
            675                 680                 685

Val Ser Ile
        690

<210> SEQ ID NO 3
<211> LENGTH: 1981
<212> TYPE: DNA
<213> ORGANISM: Arabidopsis thaliana
<220> FEATURE:
<221> NAME/KEY: misc_feature
<222> LOCATION: (0)...(0)
<223> OTHER INFORMATION: ABI1 cDNA (Genbank Accession No. X77116)
<220> FEATURE:
<221> NAME/KEY: CDS
<222> LOCATION: (432)...(1736)

<400> SEQUENCE: 3
catttcctcc ttctttctct cttctatctg tgaacaaggc acattagaac tcttcttttc      60
aactttttta ggtgtatata gatgaatcta gaaatagttt tatagttgga aattaattga     120
agagagagag atattactac accaatcttt tcaagaggtc ctaacgaatt acccacaatc     180
caggaaaccc ttattgaaat tcaattcatt tcttcttttc tgtgtttgtg attttcccgg     240
gaaatatttt tgggtatatg tctctctgtt tttgctttcc ttttttcatag gagtcatgtg     300 tttcttcttg tcttcctagc ttcttctaat aaagtccttc tcttgtgaaa atctctcgaa     360
ttttcatttt tgttccattg gagctatctt atagatcaca accagagaaa agatcaaat     420 ctttaccgtt a atg gag gaa gta tct ccg gcg atc gca ggt cct ttc agg     470
           Met Glu Glu Val Ser Pro Ala Ile Ala Gly Pro Phe Arg
           1               5                   10 cca ttc tcc gaa acc cag atg gat ttc acc ggg atc aga ttg ggt aaa     518
Pro Phe Ser Glu Thr Gln Met Asp Phe Thr Gly Ile Arg Leu Gly Lys
        15                  20                  25 ggt tac tgc aat aac caa tac tca aat caa gat tcc gag aac gga gat     566
Gly Tyr Cys Asn Asn Gln Tyr Ser Asn Gln Asp Ser Glu Asn Gly Asp
30                  35                  40                  45 cta atg gtt tcg tta ccg gag act tca tca tgc tct gtt tct ggg tca     614
Leu Met Val Ser Leu Pro Glu Thr Ser Ser Cys Ser Val Ser Gly Ser
                50                  55                  60 cat ggt tct gaa tct agg aaa gtt ttg att tct cgg atc aat tct cct     662
His Gly Ser Glu Ser Arg Lys Val Leu Ile Ser Arg Ile Asn Ser Pro
            65                  70                  75 aat tta aac atg aag gaa tca gca gct gct gat ata gtc gtc gtt gat     710
Asn Leu Asn Met Lys Glu Ser Ala Ala Ala Asp Ile Val Val Val Asp
        80                  85                  90
```

| | | |
|---|---|---|
| atc tcc gcc gga gat gag atc aac ggc tca gat att act agc gag aag<br>Ile Ser Ala Gly Asp Glu Ile Asn Gly Ser Asp Ile Thr Ser Glu Lys<br>95                             100                    105 | 758 |
| aag atg atc agc aga aca gag agt agg agt ttg ttt gaa ttc aag agt<br>Lys Met Ile Ser Arg Thr Glu Ser Arg Ser Leu Phe Glu Phe Lys Ser<br>110                  115                    120                 125 | 806 |
| gtg cct ttg tat ggt ttt act tcg att tgt gga aga aga cct gag atg<br>Val Pro Leu Tyr Gly Phe Thr Ser Ile Cys Gly Arg Arg Pro Glu Met<br>                  130                    135                 140 | 854 |
| gaa gat gct gtt tcg act ata cca aga ttc ctt caa tct tcc tct ggt<br>Glu Asp Ala Val Ser Thr Ile Pro Arg Phe Leu Gln Ser Ser Ser Gly<br>             145                    150                 155 | 902 |
| tcg atg tta gat ggt cgg ttt gat cct caa tcc gcc gct cat ttc ttc<br>Ser Met Leu Asp Gly Arg Phe Asp Pro Gln Ser Ala Ala His Phe Phe<br>160                           165                    170 | 950 |
| ggt gtt tac gac ggc cat ggc ggt tct cag gta gcg aac tat tgt aga<br>Gly Val Tyr Asp Gly His Gly Gly Ser Gln Val Ala Asn Tyr Cys Arg<br>175                           180                    185 | 998 |
| gag agg atg cat ttg gct ttg gcg gag gag ata gct aag gag aaa ccg<br>Glu Arg Met His Leu Ala Leu Ala Glu Glu Ile Ala Lys Glu Lys Pro<br>190                         195                    200               205 | 1046 |
| atg ctc tgc gat ggt gat acg tgg ctg gag aag tgg aag aaa gct ctt<br>Met Leu Cys Asp Gly Asp Thr Trp Leu Glu Lys Trp Lys Lys Ala Leu<br>                  210                    215                 220 | 1094 |
| ttc aac tcg ttc ctg aga gtt gac tcg gag att gag tca gtt gcg ccg<br>Phe Asn Ser Phe Leu Arg Val Asp Ser Glu Ile Glu Ser Val Ala Pro<br>             225                    230                 235 | 1142 |
| gag acg gtt ggg tca acg tcg gtg gtt gcc gtt gtt ttc ccg tct cac<br>Glu Thr Val Gly Ser Thr Ser Val Val Ala Val Val Phe Pro Ser His<br>                  240                    245               250 | 1190 |
| atc ttc gtc gct aac tgc ggt gac tct aga gcc gtt ctt tgc cgc ggc<br>Ile Phe Val Ala Asn Cys Gly Asp Ser Arg Ala Val Leu Cys Arg Gly<br>255                          260                    265 | 1238 |
| aaa act gca ctt cca tta tcc gtt gac cat aaa ccg gat aga gaa gat<br>Lys Thr Ala Leu Pro Leu Ser Val Asp His Lys Pro Asp Arg Glu Asp<br>270                         275                    280               285 | 1286 |
| gaa gct gcg agg att gaa gcc gca gga ggg aaa gtg att cag tgg aat<br>Glu Ala Ala Arg Ile Glu Ala Ala Gly Gly Lys Val Ile Gln Trp Asn<br>                  290                    295                 300 | 1334 |
| gga gct cgt gtt ttc ggt gtt ctc gcc atg tcg aga tcc att ggc gat<br>Gly Ala Arg Val Phe Gly Val Leu Ala Met Ser Arg Ser Ile Gly Asp<br>             305                    310                 315 | 1382 |
| aga tac ttg aaa cca tcc atc att cct gat ccg gaa gtg acg gct gtg<br>Arg Tyr Leu Lys Pro Ser Ile Ile Pro Asp Pro Glu Val Thr Ala Val<br>                  320                    325                 330 | 1430 |
| aag aga gta aaa gaa gat gat tgt ctg att ttg gcg agt gac ggg gtt<br>Lys Arg Val Lys Glu Asp Asp Cys Leu Ile Leu Ala Ser Asp Gly Val<br>335                           340                    345 | 1478 |
| tgg gat gta atg acg gat gaa gaa gcg tgt gag atg gca agg aag cgg<br>Trp Asp Val Met Thr Asp Glu Glu Ala Cys Glu Met Ala Arg Lys Arg<br>350                           355                    360               365 | 1526 |
| att ctc ttg tgg cac aag aaa aac gcg gtg gct ggg gat gca tcg ttg<br>Ile Leu Leu Trp His Lys Lys Asn Ala Val Ala Gly Asp Ala Ser Leu<br>                  370                    375                 380 | 1574 |
| ctc gcg gat gag cgg aga aag gaa ggg aaa gat cct gcg gcg atg tcc<br>Leu Ala Asp Glu Arg Arg Lys Glu Gly Lys Asp Pro Ala Ala Met Ser<br>             385                    390                 395 | 1622 |
| gcg gct gag tat ttg tca aag ctg gcg ata cag aga gga agc aaa gac<br>Ala Ala Glu Tyr Leu Ser Lys Leu Ala Ile Gln Arg Gly Ser Lys Asp<br>                  400                    405               410 | 1670 |

```
aac ata agt gtg gtg gtg gtt gat ttg aag cct cgg agg aaa ctc aag        1718
Asn Ile Ser Val Val Val Val Asp Leu Lys Pro Arg Arg Lys Leu Lys
    415                 420                 425 agc aaa ccc ttg aac tga ggcagagagg gtcctttttc ttaattttta               1766
Ser Lys Pro Leu Asn
430 aaatgaatat gggtctctcc aagaaaaagt atttactatt attaatttgt gcttatttt       1826 ttaactaaca agttataacc atatggagat aatgaagctt aatgtgttaa gctcttttgt      1886 cttgactaca ttctaaaaag ccccttgtat ttttcttccc gggctaattg taatatggtt      1946 acaacataca ttaagatgta gtattattgt ttaaa                                 1981

<210> SEQ ID NO 4
<211> LENGTH: 434
<212> TYPE: PRT
<213> ORGANISM: Arabidopsis thaliana

<400> SEQUENCE: 4

Met Glu Glu Val Ser Pro Ala Ile Ala Gly Pro Phe Arg Pro Phe Ser
1               5                   10                  15

Glu Thr Gln Met Asp Phe Thr Gly Ile Arg Leu Gly Lys Gly Tyr Cys
            20                  25                  30

Asn Asn Gln Tyr Ser Asn Gln Asp Ser Glu Asn Gly Asp Leu Met Val
        35                  40                  45

Ser Leu Pro Glu Thr Ser Ser Cys Ser Val Ser Gly Ser His Gly Ser
    50                  55                  60

Glu Ser Arg Lys Val Leu Ile Ser Arg Ile Asn Ser Pro Asn Leu Asn
65                  70                  75                  80

Met Lys Glu Ser Ala Ala Ala Asp Ile Val Val Asp Ile Ser Ala
                85                  90                  95

Gly Asp Glu Ile Asn Gly Ser Asp Ile Thr Ser Glu Lys Lys Met Ile
            100                 105                 110

Ser Arg Thr Glu Ser Arg Ser Leu Phe Glu Phe Lys Ser Val Pro Leu
        115                 120                 125

Tyr Gly Phe Thr Ser Ile Cys Gly Arg Arg Pro Glu Met Glu Asp Ala
    130                 135                 140

Val Ser Thr Ile Pro Arg Phe Leu Gln Ser Ser Ser Gly Ser Met Leu
145                 150                 155                 160

Asp Gly Arg Phe Asp Pro Gln Ser Ala Ala His Phe Phe Gly Val Tyr
                165                 170                 175

Asp Gly His Gly Gly Ser Gln Val Ala Asn Tyr Cys Arg Glu Arg Met
            180                 185                 190

His Leu Ala Leu Ala Glu Glu Ile Ala Lys Glu Lys Pro Met Leu Cys
        195                 200                 205

Asp Gly Asp Thr Trp Leu Glu Lys Trp Lys Lys Ala Leu Phe Asn Ser
    210                 215                 220

Phe Leu Arg Val Asp Ser Glu Ile Glu Ser Val Ala Pro Glu Thr Val
225                 230                 235                 240

Gly Ser Thr Ser Val Val Ala Val Phe Pro Ser His Ile Phe Val
                245                 250                 255

Ala Asn Cys Gly Asp Ser Arg Ala Val Leu Cys Arg Gly Lys Thr Ala
            260                 265                 270

Leu Pro Leu Ser Val Asp His Lys Pro Asp Arg Glu Asp Glu Ala Ala
        275                 280                 285

Arg Ile Glu Ala Ala Gly Gly Lys Val Ile Gln Trp Asn Gly Ala Arg
    290                 295                 300
```

```
Val Phe Gly Val Leu Ala Met Ser Arg Ser Ile Gly Asp Arg Tyr Leu
305                 310                 315                 320

Lys Pro Ser Ile Ile Pro Asp Pro Glu Val Thr Ala Val Lys Arg Val
            325                 330                 335

Lys Glu Asp Asp Cys Leu Ile Leu Ala Ser Asp Gly Val Trp Asp Val
            340                 345                 350

Met Thr Asp Glu Glu Ala Cys Glu Met Ala Arg Lys Arg Ile Leu Leu
        355                 360                 365

Trp His Lys Lys Asn Ala Val Ala Gly Asp Ala Ser Leu Leu Ala Asp
        370                 375                 380

Glu Arg Arg Lys Glu Gly Lys Asp Pro Ala Ala Met Ser Ala Ala Glu
385                 390                 395                 400

Tyr Leu Ser Lys Leu Ala Ile Gln Arg Gly Ser Lys Asp Asn Ile Ser
                405                 410                 415

Val Val Val Asp Leu Lys Pro Arg Arg Lys Leu Lys Ser Lys Pro
            420                 425                 430

Leu Asn

<210> SEQ ID NO 5
<211> LENGTH: 1470
<212> TYPE: DNA
<213> ORGANISM: Arabidopsis thaliana
<220> FEATURE:
<221> NAME/KEY: misc_feature
<222> LOCATION: (0)...(0)
<223> OTHER INFORMATION: ABI2 cDNA (Genbank Accession No. Y08965)
<220> FEATURE:
<221> NAME/KEY: CDS
<222> LOCATION: (51)...(1322)

<400> SEQUENCE: 5
tttttgttaa agttcaagaa agttcttttt tcttttttt tcctcctta atg gac           56
                                                     Met Asp
                                                      1 gaa gtt tct cct gca gtc gct gtt cca ttc aga cca ttc act gac cct      104
Glu Val Ser Pro Ala Val Ala Val Pro Phe Arg Pro Phe Thr Asp Pro
        5                   10                  15 cac gcc gga ctt aga ggc tat tgc aac ggt gaa tct agg gtt act tta      152
His Ala Gly Leu Arg Gly Tyr Cys Asn Gly Glu Ser Arg Val Thr Leu
    20                  25                  30 ccg gaa agt tct tgt tct ggc gac gga gct atg aaa gat tct tcc ttt      200
Pro Glu Ser Ser Cys Ser Gly Asp Gly Ala Met Lys Asp Ser Ser Phe
35                  40                  45                  50 gag atc aat aca aga caa gat tca ttg aca tca tca tct gct atg          248
Glu Ile Asn Thr Arg Gln Asp Ser Leu Thr Ser Ser Ser Ala Met
                55                  60                  65 gca ggt gtg gat atc tcc gcc gga gat gaa atc aac ggt tca gat gag      296
Ala Gly Val Asp Ile Ser Ala Gly Asp Glu Ile Asn Gly Ser Asp Glu
            70                  75                  80 ttt gat ccg aga tcg atg aat cag agt gag aag aaa gta ctt agt aga      344
Phe Asp Pro Arg Ser Met Asn Gln Ser Glu Lys Lys Val Leu Ser Arg
        85                  90                  95 aca gag agt aga agt ctg ttt gag ttc aag tgt gtt cct tta tat gga      392
Thr Glu Ser Arg Ser Leu Phe Glu Phe Lys Cys Val Pro Leu Tyr Gly
    100                 105                 110 gtg act tcg att tgt ggt aga cga cca gag atg gaa gat tct gtc tca      440
Val Thr Ser Ile Cys Gly Arg Arg Pro Glu Met Glu Asp Ser Val Ser
115                 120                 125                 130 acg att cct aga ttc ctt caa gtt tct tct agt tcg ttg ctt gat ggt      488
Thr Ile Pro Arg Phe Leu Gln Val Ser Ser Ser Ser Leu Leu Asp Gly
```

|     |     |     |     |     |     |     |     |     |     |     |     |     |     |     |     |     |
|---|---|---|---|---|---|---|---|---|---|---|---|---|---|---|---|---|
|     |     |     | 135 |     |     |     |     | 140 |     |     |     |     | 145 |     |     |     |
| cga | gtc | act | aat | gga | ttt | aat | cct | cac | ttg | agt | gct | cat | ttc | ttt | ggt | 536 |
| Arg | Val | Thr | Asn | Gly | Phe | Asn | Pro | His | Leu | Ser | Ala | His | Phe | Phe | Gly |     |
|     |     | 150 |     |     |     |     | 155 |     |     |     |     | 160 |     |     |     |     |
| gtt | tac | gat | ggc | cat | ggc | ggt | tct | cag | gta | gcg | aat | tat | tgt | cgt | gag | 584 |
| Val | Tyr | Asp | Gly | His | Gly | Gly | Ser | Gln | Val | Ala | Asn | Tyr | Cys | Arg | Glu |     |
|     | 165 |     |     |     |     | 170 |     |     |     |     | 175 |     |     |     |     |     |
| agg | atg | cat | ctg | gct | ttg | acg | gag | gag | ata | gtg | aag | gag | aaa | ccg | gag | 632 |
| Arg | Met | His | Leu | Ala | Leu | Thr | Glu | Glu | Ile | Val | Lys | Glu | Lys | Pro | Glu |     |
|     | 180 |     |     |     |     | 185 |     |     |     |     | 190 |     |     |     |     |     |
| ttt | tgt | gac | ggt | gac | acg | tgg | caa | gag | aag | tgg | aag | aag | gct | ttg | ttc | 680 |
| Phe | Cys | Asp | Gly | Asp | Thr | Trp | Gln | Glu | Lys | Trp | Lys | Lys | Ala | Leu | Phe |     |
| 195 |     |     |     |     | 200 |     |     |     |     | 205 |     |     |     |     | 210 |     |
| aac | tct | ttt | atg | aga | gtt | gac | tcg | gag | att | gaa | act | gtg | gct | cat | gct | 728 |
| Asn | Ser | Phe | Met | Arg | Val | Asp | Ser | Glu | Ile | Glu | Thr | Val | Ala | His | Ala |     |
|     |     |     |     | 215 |     |     |     |     | 220 |     |     |     |     | 225 |     |     |
| ccg | gaa | act | gtt | ggg | tct | acc | tcg | gtg | gtt | gcg | gtt | gtc | ttt | ccg | act | 776 |
| Pro | Glu | Thr | Val | Gly | Ser | Thr | Ser | Val | Val | Ala | Val | Val | Phe | Pro | Thr |     |
|     |     |     | 230 |     |     |     |     | 235 |     |     |     |     | 240 |     |     |     |
| cac | atc | ttt | gtc | gcg | aat | tgc | ggc | gac | tct | agg | gcg | gtt | ttg | tgt | cgc | 824 |
| His | Ile | Phe | Val | Ala | Asn | Cys | Gly | Asp | Ser | Arg | Ala | Val | Leu | Cys | Arg |     |
|     | 245 |     |     |     |     | 250 |     |     |     |     | 255 |     |     |     |     |     |
| ggc | aaa | acg | cca | ctc | gcg | ttg | tcg | gtt | gat | cac | aaa | ccg | gat | agg | gat | 872 |
| Gly | Lys | Thr | Pro | Leu | Ala | Leu | Ser | Val | Asp | His | Lys | Pro | Asp | Arg | Asp |     |
|     | 260 |     |     |     |     | 265 |     |     |     |     | 270 |     |     |     |     |     |
| gat | gaa | gcg | gcg | agg | ata | gaa | gct | gcc | ggt | ggg | aaa | gta | atc | cgg | tgg | 920 |
| Asp | Glu | Ala | Ala | Arg | Ile | Glu | Ala | Ala | Gly | Gly | Lys | Val | Ile | Arg | Trp |     |
| 275 |     |     |     |     | 280 |     |     |     |     | 285 |     |     |     |     | 290 |     |
| aac | ggg | gct | cgt | gta | ttt | ggt | gtt | ctc | gca | atg | tca | aga | tcc | att | ggc | 968 |
| Asn | Gly | Ala | Arg | Val | Phe | Gly | Val | Leu | Ala | Met | Ser | Arg | Ser | Ile | Gly |     |
|     |     |     |     | 295 |     |     |     |     | 300 |     |     |     |     | 305 |     |     |
| gat | aga | tac | ctt | aaa | ccg | tca | gta | att | ccg | gat | cca | gaa | gtg | act | tca | 1016 |
| Asp | Arg | Tyr | Leu | Lys | Pro | Ser | Val | Ile | Pro | Asp | Pro | Glu | Val | Thr | Ser |     |
|     |     |     | 310 |     |     |     |     | 315 |     |     |     |     | 320 |     |     |     |
| gtg | cgg | cga | gta | aaa | gaa | gat | gat | tgt | ctc | atc | tta | gca | agt | gat | ggt | 1064 |
| Val | Arg | Arg | Val | Lys | Glu | Asp | Asp | Cys | Leu | Ile | Leu | Ala | Ser | Asp | Gly |     |
|     |     | 325 |     |     |     |     | 330 |     |     |     |     | 335 |     |     |     |     |
| ctt | tgg | gat | gta | atg | aca | aac | gaa | gaa | gtg | tgc | gat | ttg | gct | cgg | aaa | 1112 |
| Leu | Trp | Asp | Val | Met | Thr | Asn | Glu | Glu | Val | Cys | Asp | Leu | Ala | Arg | Lys |     |
|     | 340 |     |     |     |     | 345 |     |     |     |     | 350 |     |     |     |     |     |
| cgg | att | tta | cta | tgg | cat | aag | aag | aac | gcg | atg | gcc | gga | gag | gct | ttg | 1160 |
| Arg | Ile | Leu | Leu | Trp | His | Lys | Lys | Asn | Ala | Met | Ala | Gly | Glu | Ala | Leu |     |
| 355 |     |     |     |     | 360 |     |     |     |     | 365 |     |     |     |     | 370 |     |
| ctt | ccg | gcg | gag | aaa | aga | gga | gaa | gga | aaa | gat | cct | gca | gca | atg | tcc | 1208 |
| Leu | Pro | Ala | Glu | Lys | Arg | Gly | Glu | Gly | Lys | Asp | Pro | Ala | Ala | Met | Ser |     |
|     |     |     |     | 375 |     |     |     |     | 380 |     |     |     |     | 385 |     |     |
| gcg | gca | gag | tat | ttg | tcg | aag | atg | gct | ttg | caa | aaa | gga | agc | aaa | gac | 1256 |
| Ala | Ala | Glu | Tyr | Leu | Ser | Lys | Met | Ala | Leu | Gln | Lys | Gly | Ser | Lys | Asp |     |
|     |     |     | 390 |     |     |     |     | 395 |     |     |     |     | 400 |     |     |     |
| aat | ata | agt | gtg | gta | gtg | gtt | gat | ttg | aag | gga | ata | agg | aaa | ttc | aag | 1304 |
| Asn | Ile | Ser | Val | Val | Val | Val | Asp | Leu | Lys | Gly | Ile | Arg | Lys | Phe | Lys |     |
|     |     | 405 |     |     |     |     | 410 |     |     |     |     | 415 |     |     |     |     |
| agc | aaa | tcc | ttg | aat | tga | aaagaaggt | ttggaagaaa | agtgaaaaaa |     |     |     |     |     |     |     | 1352 |
| Ser | Lys | Ser | Leu | Asn |     |     |     |     |     |     |     |     |     |     |     |     |
|     | 420 |     |     |     |     |     |     |     |     |     |     |     |     |     |     |     |
| aaagttttga | tggtgggtaa | aaattctctt | tagtgaaaaa | agaaagataa | aacaacaggt |     |     |     |     |     |     |     |     |     |     | 1412 |
| aataattaca | ttgtaatatt | aatttcctgc | ttaaatttgt | tatttacttt | ctcaaaaa |     |     |     |     |     |     |     |     |     |     | 1470 |

<210> SEQ ID NO 6

<211> LENGTH: 423
<212> TYPE: PRT
<213> ORGANISM: Arabidopsis thaliana

<400> SEQUENCE: 6

| | | | | | | | | | | | | | | |
|---|---|---|---|---|---|---|---|---|---|---|---|---|---|---|
| Met | Asp | Glu | Val | Ser | Pro | Ala | Val | Ala | Val | Pro | Phe | Arg | Pro | Phe | Thr |
| 1 | | | | 5 | | | | | 10 | | | | | 15 | |

Asp Pro His Ala Gly Leu Arg Gly Tyr Cys Asn Gly Glu Ser Arg Val
            20                  25                  30

Thr Leu Pro Glu Ser Ser Cys Ser Gly Asp Gly Ala Met Lys Asp Ser
        35                  40                  45

Ser Phe Glu Ile Asn Thr Arg Gln Asp Ser Leu Thr Ser Ser Ser Ser
    50                  55                  60

Ala Met Ala Gly Val Asp Ile Ser Ala Gly Asp Glu Ile Asn Gly Ser
65                  70                  75                  80

Asp Glu Phe Asp Pro Arg Ser Met Asn Gln Ser Glu Lys Lys Val Leu
                85                  90                  95

Ser Arg Thr Glu Ser Arg Ser Leu Phe Glu Phe Lys Cys Val Pro Leu
            100                 105                 110

Tyr Gly Val Thr Ser Ile Cys Gly Arg Arg Pro Glu Met Glu Asp Ser
        115                 120                 125

Val Ser Thr Ile Pro Arg Phe Leu Gln Val Ser Ser Ser Leu Leu
    130                 135                 140

Asp Gly Arg Val Thr Asn Gly Phe Asn Pro His Leu Ser Ala His Phe
145                 150                 155                 160

Phe Gly Val Tyr Asp Gly His Gly Gly Ser Gln Val Ala Asn Tyr Cys
                165                 170                 175

Arg Glu Arg Met His Leu Ala Leu Thr Glu Glu Ile Val Lys Glu Lys
            180                 185                 190

Pro Glu Phe Cys Asp Gly Asp Thr Trp Gln Glu Lys Trp Lys Lys Ala
        195                 200                 205

Leu Phe Asn Ser Phe Met Arg Val Asp Ser Glu Ile Glu Thr Val Ala
    210                 215                 220

His Ala Pro Glu Thr Val Gly Ser Thr Ser Val Val Ala Val Val Phe
225                 230                 235                 240

Pro Thr His Ile Phe Val Ala Asn Cys Gly Asp Ser Arg Ala Val Leu
                245                 250                 255

Cys Arg Gly Lys Thr Pro Leu Ala Leu Ser Val Asp His Lys Pro Asp
            260                 265                 270

Arg Asp Asp Glu Ala Ala Arg Ile Glu Ala Ala Gly Gly Lys Val Ile
        275                 280                 285

Arg Trp Asn Gly Ala Arg Val Phe Gly Val Leu Ala Met Ser Arg Ser
    290                 295                 300

Ile Gly Asp Arg Tyr Leu Lys Pro Ser Val Ile Pro Asp Pro Glu Val
305                 310                 315                 320

Thr Ser Val Arg Arg Val Lys Glu Asp Asp Cys Leu Ile Leu Ala Ser
                325                 330                 335

Asp Gly Leu Trp Asp Val Met Thr Asn Glu Glu Val Cys Asp Leu Ala
            340                 345                 350

Arg Lys Arg Ile Leu Leu Trp His Lys Lys Asn Ala Met Ala Gly Glu
        355                 360                 365

Ala Leu Leu Pro Ala Glu Lys Arg Gly Glu Gly Lys Asp Pro Ala Ala
    370                 375                 380

Met Ser Ala Ala Glu Tyr Leu Ser Lys Met Ala Leu Gln Lys Gly Ser
385                 390                 395                 400

```
Lys Asp Asn Ile Ser Val Val Val Asp Leu Lys Gly Ile Arg Lys
            405                 410                 415

Phe Lys Ser Lys Ser Leu Asn
            420

<210> SEQ ID NO 7
<211> LENGTH: 2868
<212> TYPE: DNA
<213> ORGANISM: Arabidopsis thaliana
<220> FEATURE:
<221> NAME/KEY: misc_feature
<222> LOCATION: (0)...(0)
<223> OTHER INFORMATION: ABI3 cDNA (Genbank Accession No. X68141)
<220> FEATURE:
<221> NAME/KEY: CDS
<222> LOCATION: (406)...(2568)

<400> SEQUENCE: 7
ctttgtgaac aaaacacatc tcgtatactt cagatctaga ctcgaaaatt ttagacctct      60
ttacaattgg tctttgttca tctgaagttg agaaaatag ttagcttagg tcggatcttt     120
tcatatgctt tggatcctcc ttcgtctctt ttgtataatt ttaaccttat caagagttct    180
ttttgaatct caaaagatta tatagtagta tagaaggttt atatgtatat gtatagccag     240
atagtttatg ttgtttaaag attcgatgat agccaagttg ggttaacttt ctttttcctt     300
gcctccttac tcacatacaa accctatctg tccgtacaaa atactaaaaa ccctaacttt     360
tctctctcca ccaatctagt ttattgtttc atttccactt caacg atg aaa agc ttg    417
                                                  Met Lys Ser Leu
                                                    1 cat gtg gcg gcc aac gcc gga gat ctg gct gag gat tgt gga ata ctc      465
His Val Ala Ala Asn Ala Gly Asp Leu Ala Glu Asp Cys Gly Ile Leu
 5                  10                  15                  20 ggt gga gac gct gat gat act gtt ttg atg gat gga att gat gaa gtt      513
Gly Gly Asp Ala Asp Asp Thr Val Leu Met Asp Gly Ile Asp Glu Val
                25                  30                  35 ggt aga gag atc tgg tta gat gac cat gga gga gat aat aat cat gtt      561
Gly Arg Glu Ile Trp Leu Asp Asp His Gly Gly Asp Asn Asn His Val
        40                  45                  50 cat ggt cat caa gat gat gat ttg att gtt cat cat gac cct tca atc      609
His Gly His Gln Asp Asp Asp Leu Ile Val His His Asp Pro Ser Ile
    55                  60                  65 ttc tat gga gat ctc cca acg ctt cct gat ttc cca tgc atg tcg tct      657
Phe Tyr Gly Asp Leu Pro Thr Leu Pro Asp Phe Pro Cys Met Ser Ser
70                  75                  80 tca tca tcg tct tca aca tct cca gct cct gtc aac gca atc gtc tcc      705
Ser Ser Ser Ser Ser Thr Ser Pro Ala Pro Val Asn Ala Ile Val Ser
85                  90                  95                 100 tca gcc tct tct tct tcg gca gct tct tcc tcc act tcc tca gct gct      753
Ser Ala Ser Ser Ser Ser Ala Ala Ser Ser Ser Thr Ser Ser Ala Ala
                105                 110                 115 tct tgg gct ata ttg aga tca gat gga gaa gat ccg act cca aac caa      801
Ser Trp Ala Ile Leu Arg Ser Asp Gly Glu Asp Pro Thr Pro Asn Gln
        120                 125                 130 aac caa tac gca tca gga aac tgt gac gac tct tct ggt gca ttg caa      849
Asn Gln Tyr Ala Ser Gly Asn Cys Asp Asp Ser Ser Gly Ala Leu Gln
    135                 140                 145 tcc aca gct tcc atg gag att cca tta gac agc agt caa ggt ttt ggt      897
Ser Thr Ala Ser Met Glu Ile Pro Leu Asp Ser Ser Gln Gly Phe Gly
150                 155                 160 tgc ggc gaa ggc ggt ggt gat tgc att gat atg atg gag act ttc ggg      945
Cys Gly Glu Gly Gly Gly Asp Cys Ile Asp Met Met Glu Thr Phe Gly
```

```
                165                 170                 175                 180
tac atg gat cta ctt gat agc aac gag ttc ttt gac acc tca gct ata       993
Tyr Met Asp Leu Leu Asp Ser Asn Glu Phe Phe Asp Thr Ser Ala Ile
                185                 190                 195 ttt agc caa gac gac gac acg caa aac cct aac ttg atg gac caa acc      1041
Phe Ser Gln Asp Asp Asp Thr Gln Asn Pro Asn Leu Met Asp Gln Thr
                200                 205                 210 ctt gag aga caa gaa gac cag gtc gtt gtt ccg atg atg gag aat aac      1089
Leu Glu Arg Gln Glu Asp Gln Val Val Val Pro Met Met Glu Asn Asn
                215                 220                 225 agt ggt gga gac atg caa atg atg aat tct tcc ttg gaa cag gac gat      1137
Ser Gly Gly Asp Met Gln Met Met Asn Ser Ser Leu Glu Gln Asp Asp
                230                 235                 240 gat ctc gct gct gtg ttt ttg gag tgg cta aag aac aac aag gag act      1185
Asp Leu Ala Ala Val Phe Leu Glu Trp Leu Lys Asn Asn Lys Glu Thr
245                 250                 255                 260 gtg tcg gct gag gat ttg agg aaa gta aag ata aag aaa gct acg att      1233
Val Ser Ala Glu Asp Leu Arg Lys Val Lys Ile Lys Lys Ala Thr Ile
                265                 270                 275 gaa tca gcg gca aga aga cta ggc ggt ggt aaa gaa gcg atg aag cag      1281
Glu Ser Ala Ala Arg Arg Leu Gly Gly Gly Lys Glu Ala Met Lys Gln
                280                 285                 290 ctt tta aag ctg att ctt gaa tgg gtc caa act aat cac tta caa aga      1329
Leu Leu Lys Leu Ile Leu Glu Trp Val Gln Thr Asn His Leu Gln Arg
                295                 300                 305 aga cgc acc acc acc acc acc aac ctc tct tat caa caa tca ttc          1377
Arg Arg Thr Thr Thr Thr Thr Asn Leu Ser Tyr Gln Gln Ser Phe
                310                 315                 320 caa caa gat cca ttt caa aac cct aac cct aat aac aac aac cta atc      1425
Gln Gln Asp Pro Phe Gln Asn Pro Asn Pro Asn Asn Asn Asn Leu Ile
325                 330                 335                 340 cca ccg tcc gac caa acc tgt ttc tca cct tca aca tgg gtt cct cca      1473
Pro Pro Ser Asp Gln Thr Cys Phe Ser Pro Ser Thr Trp Val Pro Pro
                345                 350                 355 cca cca caa caa caa gct ttt gtc tcg gac ccg ggt ttt gga tac atg      1521
Pro Pro Gln Gln Gln Ala Phe Val Ser Asp Pro Gly Phe Gly Tyr Met
                360                 365                 370 cct gct cca aac tat ccg cca cag cca gag ttc ctt cct tta ctt gaa      1569
Pro Ala Pro Asn Tyr Pro Pro Gln Pro Glu Phe Leu Pro Leu Leu Glu
                375                 380                 385 tct cca ccg tca tgg cca cca cca cag tct ggt ccc atg cca cat          1617
Ser Pro Pro Ser Trp Pro Pro Pro Gln Ser Gly Pro Met Pro His
                390                 395                 400 caa caa ttc ccc atg ccg cca acc tcg cag tat aat caa ttt gga gat      1665
Gln Gln Phe Pro Met Pro Pro Thr Ser Gln Tyr Asn Gln Phe Gly Asp
405                 410                 415                 420 cca aca ggt ttc aat gga tac aac atg aat ccg tac caa tat cct tat      1713
Pro Thr Gly Phe Asn Gly Tyr Asn Met Asn Pro Tyr Gln Tyr Pro Tyr
                425                 430                 435 gtt cct gca gga caa atg aga gat cag aga tta ctc cgt ttg tgt tcc      1761
Val Pro Ala Gly Gln Met Arg Asp Gln Arg Leu Leu Arg Leu Cys Ser
                440                 445                 450 tca gca act aaa gag gca aga aag aaa cgg atg gcg aga cag agg agg      1809
Ser Ala Thr Lys Glu Ala Arg Lys Lys Arg Met Ala Arg Gln Arg Arg
                455                 460                 465 ttc ttg tct cat cac cac aga cat aac aac aac aac aac aac aac aac      1857
Phe Leu Ser His His His Arg His Asn Asn Asn Asn Asn Asn Asn Asn
                470                 475                 480 aat aat cag cag aac caa acc caa atc gga gaa acc tgt gcc gcg gtg      1905
Asn Asn Gln Gln Asn Gln Thr Gln Ile Gly Glu Thr Cys Ala Ala Val
```

-continued

```
                485                 490                 495                 500
gct cca caa ctt aac ccc gtg gcc aca acc gcc acg gga ggg acc tgg    1953
Ala Pro Gln Leu Asn Pro Val Ala Thr Thr Ala Thr Gly Gly Thr Trp
                    505                 510                 515 atg tat tgg cct aat gtc ccg gca gtg ccg cct caa tta ccg cca gtg    2001
Met Tyr Trp Pro Asn Val Pro Ala Val Pro Pro Gln Leu Pro Pro Val
                520                 525                 530 atg gag act cag tta cct acc atg gac cga gct ggc tca gct tct gct    2049
Met Glu Thr Gln Leu Pro Thr Met Asp Arg Ala Gly Ser Ala Ser Ala
            535                 540                 545 atg cca cgt cag cag gtg gta cca gat cgc cgg cag gga tgg aaa cca    2097
Met Pro Arg Gln Gln Val Val Pro Asp Arg Arg Gln Gly Trp Lys Pro
        550                 555                 560 gaa aag aat ttg cgg ttt ctc ttg cag aaa gtc ttg aag caa agc gac    2145
Glu Lys Asn Leu Arg Phe Leu Leu Gln Lys Val Leu Lys Gln Ser Asp
565                 570                 575                 580 gtg ggt aac ctc gga agg atc gtt ttg cca aaa aaa gaa gct gag aca    2193
Val Gly Asn Leu Gly Arg Ile Val Leu Pro Lys Lys Glu Ala Glu Thr
                    585                 590                 595 cac ttg ccg gag cta gag gca aga gac ggc atc tct ctg gcc atg gaa    2241
His Leu Pro Glu Leu Glu Ala Arg Asp Gly Ile Ser Leu Ala Met Glu
                600                 605                 610 gac atc gga acc tct cgt gtt tgg aac atg cgc tac agg ttt tgg cct    2289
Asp Ile Gly Thr Ser Arg Val Trp Asn Met Arg Tyr Arg Phe Trp Pro
            615                 620                 625 aac aac aaa agc agg atg tat ctc ctc gag aac acc ggc gat ttt gtg    2337
Asn Asn Lys Ser Arg Met Tyr Leu Leu Glu Asn Thr Gly Asp Phe Val
        630                 635                 640 aaa acc aat ggg ctc caa gaa ggt gat ttc ata gtc ata tac tcc gac    2385
Lys Thr Asn Gly Leu Gln Glu Gly Asp Phe Ile Val Ile Tyr Ser Asp
645                 650                 655                 660 gtc aaa tgt ggc aaa tat ttg ata cga ggg gtt aaa gta aga caa ccg    2433
Val Lys Cys Gly Lys Tyr Leu Ile Arg Gly Val Lys Val Arg Gln Pro
                    665                 670                 675 agc gga caa aag ccg gag gcc cca ccg tcg tca gca gct acg aag aga    2481
Ser Gly Gln Lys Pro Glu Ala Pro Pro Ser Ser Ala Ala Thr Lys Arg
                680                 685                 690 caa aac aag tcg caa agg aac ata aac aat aac tct ccg tcg gcg aat    2529
Gln Asn Lys Ser Gln Arg Asn Ile Asn Asn Asn Ser Pro Ser Ala Asn
            695                 700                 705 gtg gtg gtc gct tca cca act tct caa act gtt aaa tga aaaacagaga    2578
Val Val Val Ala Ser Pro Thr Ser Gln Thr Val Lys
        710                 715                 720 caaaaagaaa caatataaat attattatgt accaaataag aaagagggca aaaggaaaaa    2638
atggcagcgt acccgagtgt gccacttctc gtgcatgcat gggatcttga agacaaatgg    2698
agggtcatga ttaaagctgt ttggtcaggg tccgggtttt tactccattt tttgcctttt    2758
cttgtcgagt cggttctttt ataactcttt actcttttta ccttcaggat attgtagaga    2818
tgattaattc tggaaatggt gtttgtgtta taaaaaaaaa aaaaaaaaa              2868

<210> SEQ ID NO 8
<211> LENGTH: 720
<212> TYPE: PRT
<213> ORGANISM: Arabidopsis thaliana

<400> SEQUENCE: 8

Met Lys Ser Leu His Val Ala Ala Asn Ala Gly Asp Leu Ala Glu Asp
1               5                   10                  15

Cys Gly Ile Leu Gly Gly Asp Ala Asp Asp Thr Val Leu Met Asp Gly
```

```
                 20                  25                  30
Ile Asp Glu Val Gly Arg Glu Ile Trp Leu Asp Asp His Gly Gly Asp
             35                  40                  45
Asn Asn His Val His Gly His Gln Asp Asp Leu Ile Val His His
         50                  55                  60
Asp Pro Ser Ile Phe Tyr Gly Asp Leu Pro Thr Leu Pro Asp Phe Pro
65                   70                  75                  80
Cys Met Ser Ser Ser Ser Ser Ser Thr Ser Pro Ala Pro Val Asn
                 85                  90                  95
Ala Ile Val Ser Ser Ala Ser Ser Ser Ala Ala Ser Ser Ser Thr
             100                 105                 110
Ser Ser Ala Ala Ser Trp Ala Ile Leu Arg Ser Asp Gly Glu Asp Pro
         115                 120                 125
Thr Pro Asn Gln Asn Gln Tyr Ala Ser Gly Asn Cys Asp Asp Ser Ser
         130                 135                 140
Gly Ala Leu Gln Ser Thr Ala Ser Met Glu Ile Pro Leu Asp Ser Ser
145                 150                 155                 160
Gln Gly Phe Gly Cys Gly Glu Gly Gly Asp Cys Ile Asp Met Met
                 165                 170                 175
Glu Thr Phe Gly Tyr Met Asp Leu Leu Asp Ser Asn Glu Phe Phe Asp
             180                 185                 190
Thr Ser Ala Ile Phe Ser Gln Asp Asp Thr Gln Asn Pro Asn Leu
         195                 200                 205
Met Asp Gln Thr Leu Glu Arg Gln Glu Asp Gln Val Val Pro Met
210                 215                 220
Met Glu Asn Asn Ser Gly Gly Asp Met Gln Met Met Asn Ser Ser Leu
225                 230                 235                 240
Glu Gln Asp Asp Asp Leu Ala Ala Val Phe Leu Glu Trp Leu Lys Asn
             245                 250                 255
Asn Lys Glu Thr Val Ser Ala Glu Asp Leu Arg Lys Val Lys Ile Lys
         260                 265                 270
Lys Ala Thr Ile Glu Ser Ala Ala Arg Arg Leu Gly Gly Gly Lys Glu
     275                 280                 285
Ala Met Lys Gln Leu Leu Lys Leu Ile Leu Glu Trp Val Gln Thr Asn
     290                 295                 300
His Leu Gln Arg Arg Arg Thr Thr Thr Thr Thr Asn Leu Ser Tyr
305                 310                 315                 320
Gln Gln Ser Phe Gln Gln Asp Pro Phe Gln Asn Pro Asn Pro Asn Asn
                 325                 330                 335
Asn Asn Leu Ile Pro Pro Ser Asp Gln Thr Cys Phe Ser Pro Ser Thr
             340                 345                 350
Trp Val Pro Pro Pro Gln Gln Gln Ala Phe Val Ser Asp Pro Gly
         355                 360                 365
Phe Gly Tyr Met Pro Ala Pro Asn Tyr Pro Pro Gln Pro Glu Phe Leu
         370                 375                 380
Pro Leu Leu Glu Ser Pro Pro Ser Trp Pro Pro Pro Gln Ser Gly
385                 390                 395                 400
Pro Met Pro His Gln Gln Phe Pro Met Pro Pro Thr Ser Gln Tyr Asn
                 405                 410                 415
Gln Phe Gly Asp Pro Thr Gly Phe Asn Gly Tyr Asn Met Asn Pro Tyr
             420                 425                 430
Gln Tyr Pro Tyr Val Pro Ala Gly Gln Met Arg Asp Gln Arg Leu Leu
         435                 440                 445
```

```
Arg Leu Cys Ser Ser Ala Thr Lys Glu Ala Arg Lys Arg Met Ala
        450                 455                 460
Arg Gln Arg Arg Phe Leu Ser His His His Arg His Asn Asn Asn Asn
465                 470                 475                 480
Asn Asn Asn Asn Asn Asn Gln Gln Asn Gln Thr Gln Ile Gly Glu Thr
                    485                 490                 495
Cys Ala Ala Val Ala Pro Gln Leu Asn Pro Val Ala Thr Thr Ala Thr
                500                 505                 510
Gly Gly Thr Trp Met Tyr Trp Pro Asn Val Pro Ala Val Pro Pro Gln
            515                 520                 525
Leu Pro Pro Val Met Glu Thr Gln Leu Pro Thr Met Asp Arg Ala Gly
        530                 535                 540
Ser Ala Ser Ala Met Pro Arg Gln Gln Val Val Pro Asp Arg Arg Gln
545                 550                 555                 560
Gly Trp Lys Pro Glu Lys Asn Leu Arg Phe Leu Leu Gln Lys Val Leu
                565                 570                 575
Lys Gln Ser Asp Val Gly Asn Leu Gly Arg Ile Val Leu Pro Lys Lys
                580                 585                 590
Glu Ala Glu Thr His Leu Pro Glu Leu Glu Ala Arg Asp Gly Ile Ser
            595                 600                 605
Leu Ala Met Glu Asp Ile Gly Thr Ser Arg Val Trp Asn Met Arg Tyr
        610                 615                 620
Arg Phe Trp Pro Asn Asn Lys Ser Arg Met Tyr Leu Leu Glu Asn Thr
625                 630                 635                 640
Gly Asp Phe Val Lys Thr Asn Gly Leu Gln Glu Gly Asp Phe Ile Val
                645                 650                 655
Ile Tyr Ser Asp Val Lys Cys Gly Lys Tyr Leu Ile Arg Gly Val Lys
                660                 665                 670
Val Arg Gln Pro Ser Gly Gln Lys Pro Glu Ala Pro Pro Ser Ser Ala
            675                 680                 685
Ala Thr Lys Arg Gln Asn Lys Ser Gln Arg Asn Ile Asn Asn Asn Ser
        690                 695                 700
Pro Ser Ala Asn Val Val Val Ala Ser Pro Thr Ser Gln Thr Val Lys
705                 710                 715                 720

<210> SEQ ID NO 9
<211> LENGTH: 1500
<212> TYPE: DNA
<213> ORGANISM: Arabidopsis thaliana
<220> FEATURE:
<221> NAME/KEY: misc_feature
<222> LOCATION: (0)...(0)
<223> OTHER INFORMATION: ABI4 cDNA (Genbank Accession No. AF040959)
<220> FEATURE:
<221> NAME/KEY: CDS
<222> LOCATION: (151)...(1137)

<400> SEQUENCE: 9
aatcgaccat tcacaacgat gacattcaaa cactcttcag tttcccttcc ttcttgattc      60
gtcctctcca ctattttctc caatttcttt aatctctctc tttctctctc tacttcctct     120
tcctcttctt cttcttcttc ttcttcatct atg gac cct tta gct tcc caa cat     174
                                   Met Asp Pro Leu Ala Ser Gln His
                                    1               5 caa cac aac cat ctg gaa gat aat aac caa acc cta acc cat aat aat     222
Gln His Asn His Leu Glu Asp Asn Asn Gln Thr Leu Thr His Asn Asn
     10                  15                  20 cct caa tcc gat tcc acc acc gac tca tca act tcc tcc gct caa cgc     270
Pro Gln Ser Asp Ser Thr Thr Asp Ser Ser Thr Ser Ser Ala Gln Arg
```

```
          25                  30                  35                  40
aaa cgc aaa ggc aaa ggt ggt ccg gac aac tcc aag ttc cgt tac cgt      318
Lys Arg Lys Gly Lys Gly Gly Pro Asp Asn Ser Lys Phe Arg Tyr Arg
                        45                  50                  55 ggc gtt cga caa aga agc tgg ggc aaa tgg gtc gcc gag atc cga gag      366
Gly Val Arg Gln Arg Ser Trp Gly Lys Trp Val Ala Glu Ile Arg Glu
                60                  65                  70 cca cgt aag cgc act cgc aag tgg ctt ggt act ttc gca acc gcc gaa      414
Pro Arg Lys Arg Thr Arg Lys Trp Leu Gly Thr Phe Ala Thr Ala Glu
            75                  80                  85 gac gcc gca cgt gcc tac gac cgg gct gcc gtt tac cta tac ggg tca      462
Asp Ala Ala Arg Ala Tyr Asp Arg Ala Ala Val Tyr Leu Tyr Gly Ser
        90                  95                 100 cgt gct cag ctc aac tta acc cct tcg tct cct tcc tcc gtc tct tcc      510
Arg Ala Gln Leu Asn Leu Thr Pro Ser Ser Pro Ser Ser Val Ser Ser
105                 110                 115                 120 tct tcc tcc tcc gtc tcc gcc gct tct tct cct tcc acc tcc tct tcc      558
Ser Ser Ser Ser Val Ser Ala Ala Ser Ser Pro Ser Thr Ser Ser Ser
                    125                 130                 135 tcc act caa acc cta aga cct ctc ctc cct cgc ccc gcc gcc gcc acc      606
Ser Thr Gln Thr Leu Arg Pro Leu Leu Pro Arg Pro Ala Ala Ala Thr
                140                 145                 150 gta gga gga gga gcc aac ttt ggt ccg tac ggt atc cct ttt aac aac      654
Val Gly Gly Gly Ala Asn Phe Gly Pro Tyr Gly Ile Pro Phe Asn Asn
            155                 160                 165 aac atc ttc ctt aat ggt ggg acc tct atg tta tgc cct agt tat ggt      702
Asn Ile Phe Leu Asn Gly Gly Thr Ser Met Leu Cys Pro Ser Tyr Gly
        170                 175                 180 ttt ttc cct caa caa caa caa caa caa aat cag atg gtc cag atg gga      750
Phe Phe Pro Gln Gln Gln Gln Gln Gln Asn Gln Met Val Gln Met Gly
185                 190                 195                 200 caa ttc caa cac caa cag tat cag aat ctt cat tct aat act aac aat      798
Gln Phe Gln His Gln Gln Tyr Gln Asn Leu His Ser Asn Thr Asn Asn
                    205                 210                 215 aac aag att tct gac atc gag ctc act gat gtt ccg gta act aat tcg      846
Asn Lys Ile Ser Asp Ile Glu Leu Thr Asp Val Pro Val Thr Asn Ser
                220                 225                 230 act tcg ttt cat cat gag gtg gcg tta ggg cag gaa caa gga gga agt      894
Thr Ser Phe His His Glu Val Ala Leu Gly Gln Glu Gln Gly Gly Ser
            235                 240                 245 ggg tgt aat aat aat agt tcg atg gag gat ttg aac tct cta gct ggt      942
Gly Cys Asn Asn Asn Ser Ser Met Glu Asp Leu Asn Ser Leu Ala Gly
        250                 255                 260 tcg gtg ggt tcg agt cta tca ata act cat cca ccg ccg ttg gtt gat      990
Ser Val Gly Ser Ser Leu Ser Ile Thr His Pro Pro Pro Leu Val Asp
265                 270                 275                 280 ccg gta tgt tct atg ggt ctg gat ccg ggt tat atg gtt gga gat gga     1038
Pro Val Cys Ser Met Gly Leu Asp Pro Gly Tyr Met Val Gly Asp Gly
                    285                 290                 295 tct tcg acc att tgg cct ttt gga gga gaa gaa gaa tat agt cat aat     1086
Ser Ser Thr Ile Trp Pro Phe Gly Gly Glu Glu Glu Tyr Ser His Asn
                300                 305                 310 tgg ggg agt att tgg gat ttt att gat ccc atc ttg ggg gaa ttc tat     1134
Trp Gly Ser Ile Trp Asp Phe Ile Asp Pro Ile Leu Gly Glu Phe Tyr
            315                 320                 325 taa tttgtttttg tggaagatca tattatatac gatgagcatc cctaaggtcg          1187
gtcaagagca ttggagattc attgttgaga ggaatcaaag agattgcatt ctatgaggag   1247
ctctgcatgc aaaattttgg aggattttttt tactacctat agataaaat aagagggtat  1307
```

-continued

```
tttattatt tttttgaaga tttttatttt caaggaattc gtaaaagaga ttacggttcc   1367
aataaagtat gtatatgtgg aagagaatcg gaggagatgg tggaaagttg tatgggaatt   1427
ttattggttc aacacttcct tcacagtgtg cctaccttaa tatataatta ttgataggat   1487
atgataattt ctg                                                     1500
```

<210> SEQ ID NO 10
<211> LENGTH: 328
<212> TYPE: PRT
<213> ORGANISM: Arabidopsis thaliana

<400> SEQUENCE: 10

```
Met Asp Pro Leu Ala Ser Gln His Gln His Asn His Leu Glu Asp Asn
 1               5                  10                  15

Asn Gln Thr Leu Thr His Asn Asn Pro Gln Ser Asp Ser Thr Thr Asp
            20                  25                  30

Ser Ser Thr Ser Ser Ala Gln Arg Lys Arg Lys Gly Lys Gly Gly Pro
        35                  40                  45

Asp Asn Ser Lys Phe Arg Tyr Arg Gly Val Arg Gln Arg Ser Trp Gly
    50                  55                  60

Lys Trp Val Ala Glu Ile Arg Glu Pro Arg Lys Arg Thr Arg Lys Trp
65                  70                  75                  80

Leu Gly Thr Phe Ala Thr Ala Glu Asp Ala Ala Arg Ala Tyr Asp Arg
                85                  90                  95

Ala Ala Val Tyr Leu Tyr Gly Ser Arg Ala Gln Leu Asn Leu Thr Pro
            100                 105                 110

Ser Ser Pro Ser Ser Val Ser Ser Ser Ser Val Ser Ala Ala
        115                 120                 125

Ser Ser Pro Ser Thr Ser Ser Ser Thr Gln Thr Leu Arg Pro Leu
    130                 135                 140

Leu Pro Arg Pro Ala Ala Ala Thr Val Gly Gly Gly Ala Asn Phe Gly
145                 150                 155                 160

Pro Tyr Gly Ile Pro Phe Asn Asn Ile Phe Leu Asn Gly Gly Thr
                165                 170                 175

Ser Met Leu Cys Pro Ser Tyr Gly Phe Phe Pro Gln Gln Gln Gln
            180                 185                 190

Gln Asn Gln Met Val Gln Met Gly Gln Phe Gln His Gln Gln Tyr Gln
        195                 200                 205

Asn Leu His Ser Asn Thr Asn Asn Lys Ile Ser Asp Ile Glu Leu
    210                 215                 220

Thr Asp Val Pro Val Thr Asn Ser Thr Ser Phe His His Glu Val Ala
225                 230                 235                 240

Leu Gly Gln Glu Gln Gly Gly Ser Gly Cys Asn Asn Asn Ser Ser Met
                245                 250                 255

Glu Asp Leu Asn Ser Leu Ala Gly Ser Val Gly Ser Ser Leu Ser Ile
            260                 265                 270

Thr His Pro Pro Pro Leu Val Asp Pro Val Cys Ser Met Gly Leu Asp
        275                 280                 285

Pro Gly Tyr Met Val Gly Asp Gly Ser Ser Thr Ile Trp Pro Phe Gly
    290                 295                 300

Gly Glu Glu Glu Tyr Ser His Asn Trp Gly Ser Ile Trp Asp Phe Ile
305                 310                 315                 320

Asp Pro Ile Leu Gly Glu Phe Tyr
                325
```

```
<210> SEQ ID NO 11
<211> LENGTH: 286
<212> TYPE: DNA
<213> ORGANISM: Glycine max
<220> FEATURE:
<221> NAME/KEY: promoter
<222> LOCATION: (0)...(0)
<223> OTHER INFORMATION: Oleosin promoter (Genbank Accession No. U71381)

<400> SEQUENCE: 11
actaatttat gtaatgtgat ttcaataagt gaggtaaact ccgattgatt gaagatacca      60
ccaacaccaa caccaccacc acctgcgaaa ctgtacgtat ctcaattgtc cttaataaaa     120
atgtaaatag tacattattc tccttgcctg tcattattta tgtgccccca gcttaatttt     180
tctgatgtac ttaacccagg gcaaaactga acaagttcc tcatgcaaag ccccaactca      240
tcatgcatca tgtaccgtgt catcatccag caactccact tttgca                   286

<210> SEQ ID NO 12
<211> LENGTH: 940
<212> TYPE: DNA
<213> ORGANISM: Brassica juncea
<220> FEATURE:
<221> NAME/KEY: promoter
<222> LOCATION: (0)...(0)
<223> OTHER INFORMATION: Oleosin promoter (Genbank Accession No.
      AF134411)

<400> SEQUENCE: 12
tctagaactt tcgggataaa gcaatcacct ggcgattcaa cgtggtcgga tcatgacgtt      60
cccagaagac atcgagtaag ctctcgaagc tgacctcttg cggatcgtac tgaacccgaa     120
caatctcgtt atgtcccgtc gtctccgaac agacatcctc gtatctcgga ttatcgacta    180
atccatggct ataccccaacc tccgtcttcg tcacgcctgg aaccctctgg tacgccaatt    240
ccgctcccca gaaacaaccg cgcccgaatt gcgcgaattg ctgacctggg agacggaaca     300
tcgtcgtcgg gtccttgcgc gattgcggcg gaagccgggt cgggttgggg acgaaaccga    360
atccgagcct ggtgaatagg ttgttcatcg gagatttata gacggagatg gatctagcgt    420
tttgggaaag ggaagtggtt tggctctttt ggatagagag agtgcagctt tggagagaga    480
ctggagaggt ttagagagag acgcggcgga gattaccgga ggagaggcga cgagagatag    540
cattatcgaa gggaagggag aaagagtgac gtggagaaat aagaaccgt taagagtcgg     600 atatttatta tattaaaagc ccaatgggcc taaacccatt taaacaagac aagataaatg    660
ggccgtgtgg taacagagtg ttacgttcgg cttcaaatgc caacgccata ggaacaaaac    720
aaacgtgtcc tcaagtaaac ccctgccgtt tacacctcaa tgactgcatg gtgaagccat    780
taacacgtgg cgtaggatgc atgacgacgc cattgacacc tgactttctt cccttctctt    840
catatatctc taatcaattc aactactcac agtcatagct attcggaaaa tacatacaca    900
tccttttctc ttcgatctct ctcaattcac aagaagcaaa                         940

<210> SEQ ID NO 13
<211> LENGTH: 807
<212> TYPE: DNA
<213> ORGANISM: Hordeum vulgare
<220> FEATURE:
<221> NAME/KEY: promoter
<222> LOCATION: (0)...(0)
<223> OTHER INFORMATION: lpt2 promoter

<400> SEQUENCE: 13
gatctcgatg tgtagtctac gagaagggtt aaccgtctct tcgtgagaat aaccgtggcc     60
```

```
taaaaataag ccgatgagga taaataaaat gtggtggtac agtacttcaa gaggtttact        120
catcaagagg atgcttttcc gatgagctct agtagtacat cggacctcac atacctccat        180
tgtggtgaaa tattttgtgc tcatttagtg atgggtaaat tttgtttatg tcactctagg        240
ttttgacatt tcagttttgc cactcttagg ttttgacaaa taatttccat tccgcggcaa        300
aagcaaaaca attttatttt acttttacca ctcttagctt tcacaatgta tcacaaatgc        360
cactctagaa attctgttta tgccacagaa tgtgaaaaaa aacactcact tatttgaagc        420
caaggtgttc atggcatgga aatgtgacat aaagtaacgt tcgtgtataa gaaaaaattg        480
tactcctcgt aacaagagac ggaaacatca tgagacaatc gcgtttggaa ggctttgcat        540
cacctttgga tgatgcgcat gaatggagtc gtctgcttgc tagccttcgc ctaccgccca        600
ctgagtccgg gcggcaacta ccatcggcga acgacccagc tgacctctac cgaccggact        660
tgaatgcgct accttcgtca gcgacgatgg ccgcgtacgc tggcgacgtg ccccccgcatg       720 catggcggca catggcgagc tcagaccgtg cgtggctggc tacaaatacg taccccgtga        780
gtgccctagc tagaaactta cacctgc                                            807
```